(12) United States Patent
Kwong

(10) Patent No.: US 12,336,512 B2
(45) Date of Patent: Jun. 24, 2025

(54) SYSTEMS AND METHODS FOR PROVIDING AND ASSOCIATING DATA FROM PET EXPERT INTERACTIONS WITH PET PROFILES

(71) Applicant: Mars, Incorporated, McLean, VA (US)

(72) Inventor: Kelvin Kwong, San Francisco, CA (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 18/622,300

(22) Filed: Mar. 29, 2024

(65) Prior Publication Data
US 2024/0324559 A1    Oct. 3, 2024

Related U.S. Application Data

(60) Provisional application No. 63/493,673, filed on Mar. 31, 2023.

(51) Int. Cl.
| | | |
|---|---|---|
| *A01K 29/00* | (2006.01) | |
| *G16H 10/60* | (2018.01) | |
| *G16H 80/00* | (2018.01) | |

(52) U.S. Cl.
CPC .......... *A01K 29/005* (2013.01); *G16H 10/60* (2018.01); *G16H 80/00* (2018.01)

(58) Field of Classification Search
CPC ....... A01K 29/005; G16H 10/60; G16H 80/00
See application file for complete search history.

(56) References Cited

U.S. PATENT DOCUMENTS

| | | | |
|---|---|---|---|
| 2014/0052463 A1* | 2/2014 | Cashman | G06Q 10/1095 705/2 |
| 2014/0267299 A1 | 9/2014 | Couse | |
| 2015/0066520 A1* | 3/2015 | Leon | G16H 10/20 705/2 |
| 2015/0294072 A1 | 10/2015 | Lyle et al. | |
| 2016/0063188 A1* | 3/2016 | Thornberry | H04L 63/08 705/3 |
| 2017/0039329 A1* | 2/2017 | Marshall, Dvm | G06Q 40/08 |
| 2018/0349852 A1* | 12/2018 | Marshall, Dvm | G06Q 40/08 |
| 2020/0352139 A1* | 11/2020 | Maung | G06Q 10/02 |
| 2020/0381119 A1 | 12/2020 | Gibbs et al. | |
| 2020/0411145 A1* | 12/2020 | Oda | G16H 10/60 |
| 2021/0151173 A1* | 5/2021 | Fukuda | G16H 40/20 |

(Continued)

OTHER PUBLICATIONS

International Search Report issued in International Application No. PCT/US2024/022384 dated Jun. 4, 2024 (12 pages).

*Primary Examiner* — Daryl C Pope
(74) *Attorney, Agent, or Firm* — Bookoff McAndrews, PLLC

(57) ABSTRACT

A method performed by at least one processor of a platform includes receiving from a first system a first data set associated with an interaction between a pet owner and an expert relating to care of a pet hosted via the first system, updating pet profile data associated with the pet based on the first data set, determining a portion of the pet profile data including the first dataset associated with a second system, and transmitting the portion of the pet profile data to the second system. The second system is configured to generate content to provide to the pet owner based on the portion of the pet profile data.

16 Claims, 17 Drawing Sheets

(56) References Cited

U.S. PATENT DOCUMENTS

| | | | |
|---|---|---|---|
| 2022/0051764 A1* | 2/2022 | Porter | G16H 70/20 |
| 2022/0125022 A1 | 4/2022 | Adams | |
| 2023/0068122 A1* | 3/2023 | Gonzalez | G06Q 10/02 |
| 2023/0354782 A1* | 11/2023 | Hegde | G06F 16/9554 |
| 2023/0404041 A1* | 12/2023 | Klein | A01K 27/001 |
| 2024/0172967 A1* | 5/2024 | Carson | G16H 50/20 |

* cited by examiner

SYSTEMS AND METHODS FOR PROVIDING AND ASSOCIATING DATA FROM PET EXPERT INTERACTIONS WITH PET PROFILES

CROSS-REFERENCE TO RELATED APPLICATION(S)

This application claims the benefit of priority to U.S. Provisional Application No. 63/493,673, filed on Mar. 31, 2023, the entirety of which is incorporated herein by reference.

TECHNICAL FIELD

The present disclosure generally relates to systems and methods for providing and collecting data from interaction sessions, and more particularly to systems and methods for associating data collected from interaction sessions between pet experts and pet owners to associate with pet profiles.

BACKGROUND

The nature of pet ownership incurs a substantial burden in creating, managing, and tracking all the different types of pet data. Current solutions to alleviate the burden of a pet owner are generic, inefficient, and are not specifically tailored towards the pet owner's needs. Moreover, pet owners may employ many independent and/or disjointed systems in managing their pets' lives. Thus, pertinent information that is raised in one setting (e.g., a veterinary office) may be lost, forgotten, or otherwise be unavailable for use in a different setting (e.g., a pet content website). Conventional techniques fail to provide a single personalized destination for the data management needs of a pet owner and the pet owner's pets.

This disclosure is directed to addressing the above-referenced challenges. The background description provided herein is for the purpose of generally presenting the context of the disclosure. Unless otherwise indicated herein, the materials described in this section are not admitted to be prior art, or suggestions of the prior art, by inclusion in this section.

SUMMARY OF THE DISCLOSURE

According to certain aspects of the disclosure, methods and systems are disclosed for associating data collected from interaction sessions between pet experts and pet owners to associate with pet profiles. Some embodiments are directed to a method performed by at least one processor of a platform. The method comprises receiving, from a first system by the at least one processor, a first data set associated with an interaction between a pet owner and an expert relating to care of a pet hosted via the first system; updating, by the at least one processor, pet profile data associated with the pet based on the first data set; determining, by the at least one processor, a portion of the pet profile data associated with a second system, the portion of the pet profile data including the first data set; and transmitting, by the at least one processor, the portion of the pet profile data to the second system, wherein the second system is configured to generate content to provide to the pet owner based on the portion of the pet profile data.

Other embodiments are directed to a computer system comprising at least one memory having processor-readable instructions stored therein, and at least one processor configured to access the memory and execute the processor-readable instructions, which when executed by the processor configure the processor to perform a plurality of functions. The plurality of functions comprises functions for receiving, from a first system, a first data set associated with an interaction between a pet owner and an expert relating to care of a pet hosted via the first system; updating pet profile data associated with the pet based on the first data set; determining a portion of the pet profile data associated with a second system, the portion of the pet profile data including the first data set; and transmitting the portion of the pet profile data to the second system, wherein the second system is configured to generate content to provide to the pet owner based on the portion of the pet profile data.

Other embodiments of the present disclosure are directed to a non-transitory computer-readable medium containing instructions that, when executed by at least one processor, configure the at least one processor to perform receiving, from a first system, a first data set associated with an interaction between a pet owner and an expert relating to care of a pet hosted via the first system; updating pet profile data associated with the pet based on the first data set; determining a portion of the pet profile data associated with a second system, the portion of the pet profile data including the first data set; and transmitting the portion of the pet profile data to the second system, wherein the second system is configured to generate content to provide to the pet owner based on the portion of the pet profile data.

It is to be understood that both the foregoing general description and the following detailed description are exemplary and explanatory only and are not restrictive of the disclosed embodiments.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
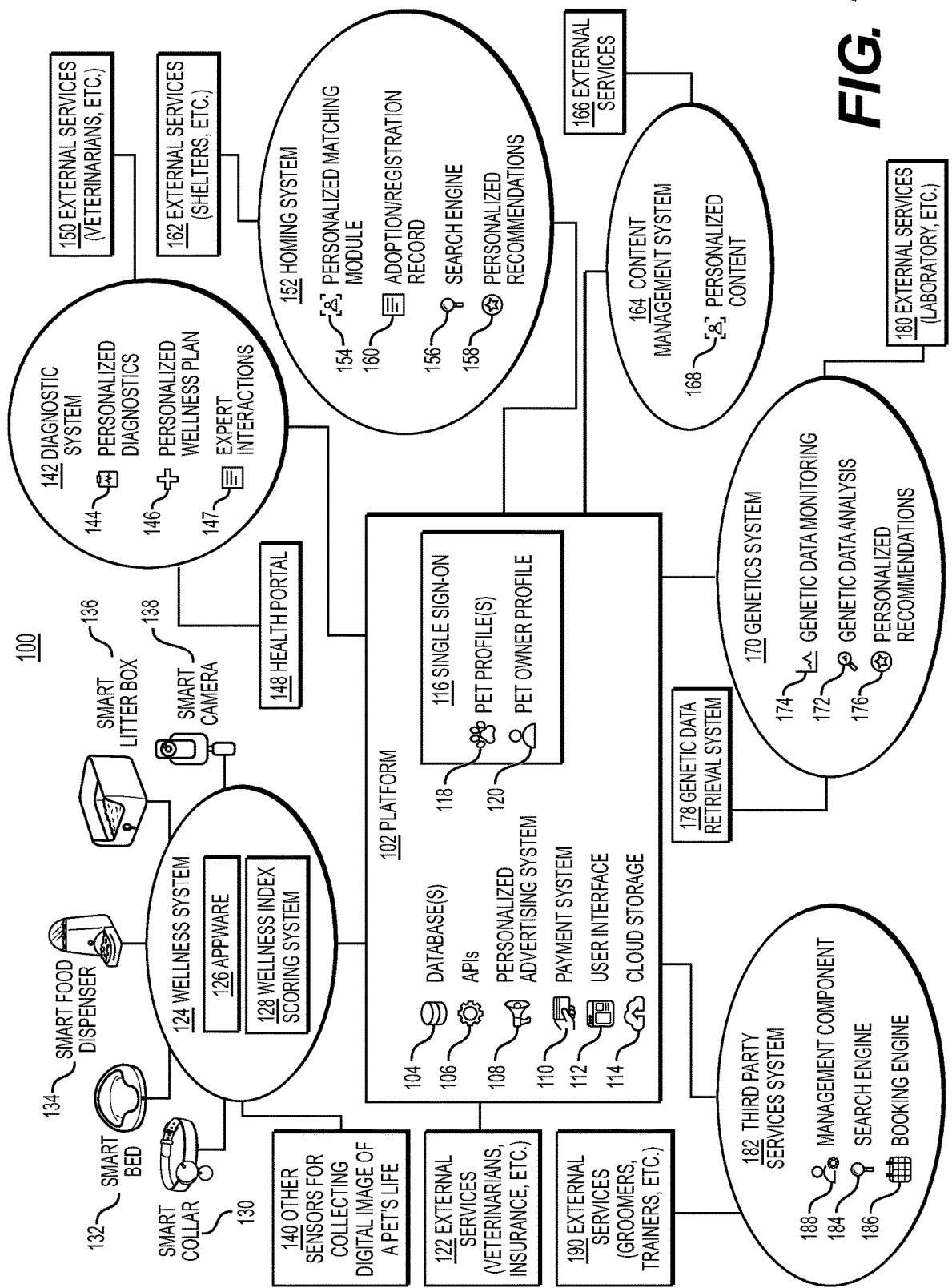
FIG. 1 depicts an exemplary platform environment, according to one or more embodiments.

According to certain aspects of the disclosure, methods and systems are disclosed for an integrated electronic pet platform. Conventional techniques may not be suitable because conventional techniques may rely on a pet owner to manually track all of the pet's data. Such techniques may involve incompatible platforms, many username and password combinations, and may also involve the pet owner misplacing the contents of the pet's data.

The pet ownership process may involve the creation, management, and storage of a large amount of pet data. A pet owner may begin to acquire pet data during the pet search process. Throughout the lifetime of the pet, the pet owner will continue to accrue important pet data, such as vaccination records, pet activity data, analysis of the pet's genetic data, and the like. However, most sources of the pet data are independent of each other, meaning these sources cannot interact with one another in a manner that allows aggregation and sharing of pet data. For example, various existing systems may generate and/or store pet data in different, incompatible formats, so even if those systems can be accessed from the same device (e.g., a smart phone), data from one system could not be shared with and used by another system. For example, information obtained from an adoption and/or registration record of a pet provided by a shelter, for example, may not be in a format compatible with systems operated by the pet's veterinarian. Such system incompatibility results in the pet owner bearing the substantial burden of sharing important information between various incompatible systems. This necessitates remembrance of a multitude of login credentials, and diligence in keeping information up to date across the various platforms. This existing methodology is particularly cumbersome because such information (which may include both paper and digital records) is susceptible to being lost, misplaced, or forgotten by the pet owner. Furthermore, pet owners may not appreciate the importance of certain data, particularly data concerning their pets' health, and therefore may fail to provide potentially beneficial data to care providers such as veterinarians.

A need exists for an integrated hardware, software, and diagnostic solution for virtualizing a pet's information, as well as providing a centralized repository. Such a solution allows for the tracking of pet owners and pets, an efficient transfer of pet data from a collection point to external providers, personalization, pet diagnostics, and the ability to scale the pet data collection depending on how many pets belong to a pet owner. Furthermore, a need exists for an integrated hardware and software solution for aggregating pet data and sharing such data between various, disjointed systems both with and without pet owner intervention. Furthermore, a need exists for an integrated hardware and software solution for recording and aggregating data from interactions with pet experts and/or smart devices to subsequently provide this data to other relevant systems.

Moreover, a need exists for systems that allow pet owners to make informed health decisions for their pets without undue trips to an in-person veterinarian. In-person veterinary appointments can be time-consuming and costly for pet owners, and may be uncomfortable for pets. Additionally, pet owners often are uncertain whether their pet's health and/or behavior warrants veterinarian attention. Pet owners' lack of expertise in medical/behavioral issues can cause, one the one hand, overuse of in-person veterinary visits for non-serious conditions, and on the other hand, allowing potentially serious issues to linger and worsen due to avoidance of in-person veterinary care. Thus, a need exists for remote, online, and/or virtual interactions with experts that serve as an intermediary step in pet health evaluations. Such interactions, during which the pet owner may receive an expert's opinion on the need for in-person veterinary care, may eliminate unnecessary in-person veterinarian visits, but encourage prompt veterinarian attention when a pet's behavior or condition warrants the same.

As will be discussed in more detail below, in various embodiments, systems and methods are described for providing and associating data from pet expert interactions with pet profiles. The systems and methods may receive a first data set from a first system that is associated with an interaction between a pet owner and an expert relating to care of a pet hosted via the first system. The systems and methods may then update pet profile data associated with the pet based on the first data set. The systems and methods may then determine a portion of the pet profile data associated with a second system, where the portion of the pet profile data may include the first data set. The systems and methods may then transmit the portion of the pet profile data to the second system. In some examples, the second system is then configured to generate content to provide to the pet owner based on the portion of the pet profile data.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, a term such as "user," or the like, generally encompasses a future pet owner, future pet owners, pet owner, and/or pet owners. A term such as "pet," or the like, generally encompasses a domestic animal, such as a domestic canine, feline, rabbit, ferret, horse, cow, or the like. In exemplary embodiments, "pet" may refer to a canine.

Exemplary Platform Environment

FIG. 1 depicts an exemplary platform environment 100 that may be utilized with the techniques presented herein. More specifically, environment 100 may provide an integrated hardware and software platform 102 for improving pet digitalization by centralizing the pet's information.

The platform 102 may communicate with one or more external systems that may collect, manage, and store different types of pet data and/or pet owner data. The platform 102 may retrieve the pet data and/or pet owner data from the one or more external systems via APIs 106. In some embodiments, the platform 102 may store the pet data and/or the pet owner data. For example, the platform 102 may store the pet data in pet profile(s) 118. Additionally, for example, the platform 102 may store the pet owner data in a pet owner profile 120. The one or more external systems may include at least one of a wellness system 124, a diagnostic system 142, a homing system 152, a content management system 164, a genetics system 170, and/or a third party services system 182. Such external systems are described in more detail below.

The platform 102 may also communicate with one or more external services. In some embodiments, the platform 102 may communicate with the one or more external services via APIs 106. External services 122 may include, for example, one or more third party and/or auxiliary systems that integrate and/or communicate with the platform 102 in performing various pet tasks. For example, the external services 122 may include at least one of: a veterinarian, a pet behaviorist, a pet nutritionist, a pet insurance agency, a pet service provider, and the like.

The platform 102 may include database(s) 104 and/or cloud storage 114 that may store information corresponding to one or more pets and/or one or more pet owners. For example, the database(s) 104 and/or cloud storage 114 may store the pet profile(s) 118 and/or the pet owner profile 120. The database(s) 104 and/or the cloud storage 114 may be located internally or externally to platform 102.

The platform 102 may include a personalized advertising system 108 and/or a payment system 110. The personalized advertising system 108 may create and/or display personalized advertisements to the user. For example, the personalized advertisements may be created based on information contained in the pet profile(s) 118 and/or the pet owner profile 120. In some embodiments, the personalized advertising system 108 may display the personalized advertisements on a user interface 112 of the platform 102. The payment system 110 may allow the user to create a financial account for a pet and/or perform financial transactions for pet services and/or pet goods (e.g., using pet owner digital wallet 216).

The platform 102 may include a single sign-on 116. The single sign-on 116 may include a unique identifier that may correspond to the pet profile(s) 118 and/or the pet owner profile 120. Each of the pet profile(s) 118 may include information corresponding to a particular pet. The pet owner profile 120 may include information corresponding to a particular pet owner. Additionally, the pet owner profile 120 and/or the pet profile(s) 118 may each have a corresponding avatar and/or virtual presence. The avatar and/or virtual presence may include different attributes that are shared by the pet owner and/or pets. The pet profile(s) 118 and the pet owner profile 120 are described in further detail in the description of FIG. 2.

Wellness System

The wellness system 124 may collect, manage, and/or display wellness data of a pet. The wellness system 124 may be an internal component or an external component of the platform 102, where the wellness system 124 may communicate with the platform 102 via APIs 106.

The wellness system 124 may collect data from one or more smart devices. The wellness system 124 may communicate with the one or more smart devices via one or more APIs. Additionally, in some embodiments, the wellness system 124 may use appware 126 to facilitate the communication and/or the management of the one or more smart devices. For example, appware 126 may communicate with one or more smart devices that may run on an external system. Additionally, for example, appware 126 may run on a user device, where the appware 126 provides a user interface to display the data collected by the one or more smart devices. In some embodiments, appware 126 may manage one or more smart devices. The wellness system 124 may communicate with the one or more smart devices by sending one or more requests to the one or more smart devices. The requests may ask the one or more smart devices to send collected wellness data to the wellness system 124. In some embodiments, the one or more smart devices may automatically send wellness data to the wellness system 124. For example, the one or more smart devices may send the wellness data to the wellness system 124 at regular time intervals (e.g., every 30 seconds, every hour, every day, and the like) and/or whenever new wellness data is collected. In some embodiments, the wellness system 124 may store the wellness data in an internal or external storage. For example, the wellness system 124 may store the wellness data in the database(s) 104 and/or the cloud storage 114. Additionally, or alternatively, for example, the wellness system 124 may store the wellness data in the pet profile(s) 118 and/or the pet owner profile 120.

Upon receiving the wellness data from the one or more smart devices, a wellness index scoring system 128 may analyze the wellness data to determine a wellness score. The wellness index scoring system 128 may update the wellness score, where the updating is based on the most recently received wellness data. In some embodiments, the wellness index scoring system 128 may store the wellness score in one or more databases (e.g., the database(s) 104) and/or cloud storage (e.g., the cloud storage 114). For example, the wellness score may be stored in the pet profile(s) 118 and/or the pet owner profile 120. Additionally, or alternatively, the wellness system 124 may display the wellness score to the user. For example, the wellness system 124 may display the wellness score on a user interface of a user device. This may be accomplished by utilizing the appware 126. Additionally, or alternatively, the wellness system 124 may display the wellness score on one or more of the smart devices.

Example smart devices may include at least one of: a smart collar 130, a smart bed 132, a smart food dispenser 134, a smart litter box 136, a smart camera 138, and/or any other sensors 140 for collecting a digital image of a pet's life.

The smart collar 130 may include a device and/or a sensor that may attach to a pet. For example, the smart collar 130 may attach around the pet's neck The smart collar 130 may detect a pet's activity, location, and eating information, such as physical activity, location, eating habits, drinking habits, and the like. The smart collar 130 may collect the activity, location, and eating information of the pet and send such information to the wellness system 124. In some embodiments, the smart collar 130 may automatically send the activity, location, and eating information to the wellness system 124 after a set period of time. In some embodiments, the smart collar 130 may send the activity, location, and eating information in response to a request from the wellness system 124.

The smart bed 132 may include a device and/or a sensor that may be included in a pet bed. The smart bed 132 may track sleeping information corresponding to the pet. The sleeping information may include the amount of time a pet sleeps in the smart bed 132, how frequently the pet gets up from the smart bed 132, if the pet tosses and turns while sleeping, and the like. The smart bed 132 may send such information to the wellness system 124. In some embodiments, the smart bed 132 may automatically send the sleeping information to the wellness system 124 after a set period of time. In some embodiments, the smart bed 132 may send the sleeping information in response to a request from the wellness system 124.

The smart food dispenser 134 may include a device and/or a sensor that may be included in a pet food feeder. The smart food dispenser 134 may track how much food is dispensed for the pet to eat. The smart food dispenser 134 may send such food dispensing information to the wellness system 124. In some embodiments, the smart food dispenser 134 may automatically send the food dispensing information to the wellness system 124 after a set period of time. In some embodiments, the smart food dispenser 134 may send the food dispensing information in response to a request from the wellness system 124.

The smart litter box 136 may include a device and/or a sensor that may be included in a litter box. The smart litter box 136 may track a pet's litter box information. The litter box information may include at least one of: how frequently the pet uses the smart litter box 136, what the pet does in the smart litter box 136, and the like. In some embodiments, the smart litter box 136 may automatically send the litter box information to the wellness system 124. In some embodiments, the smart litter box 136 may automatically send the litter box information to the wellness system 124 after a set period of time. In some embodiments, the smart litter box 136 may send the litter box information in response to a request from the wellness system 124.

The smart camera 138 may include a device and/or a sensor that may be included in a camera. The smart camera 138 may capture behavior information of a pet. The pet's behavior information may include physical activity, eating food from the pet's food dish, eating food from a source different from the pet's food dish, drinking from the pet's drinking dish, drinking from a source different from the pet's drinking dish, and the like. In some embodiments, the smart camera 138 may automatically send the behavior information to the wellness system 124 after a set period of time. In some embodiments, the smart camera 138 may send the behavior information in response to a request from the wellness system 124.

The other sensors 140 for collecting a digital image of a pet's life may include one or more devices and/or one or more sensors that collect data for a digital image of the pet's life. Example collected data may include information regarding the pet's eating behavior, sleeping behavior, drinking behavior, playing behavior, and the like. In some embodiments, the other sensors 140 may automatically send the collected data to the wellness system 124 after a set period of time. In some embodiments, the other sensors 140 may send the collected data in response to a request from the wellness system 124.

Diagnostic System

The diagnostic system 142 may manage a pet's health information and provide personalized diagnostics 144 and/or a personalized wellness plan 146 to the user. Additionally, the diagnostic system 142 may facilitate interactions between pet experts and pet owners, hereinafter referred to as expert interactions 147. The diagnostic system 142 may be an internal component or an external component of the platform 102, where the diagnostic system 142 may communicate with the platform 102 via APIs 106.

The diagnostic system 142 may manage a pet's health information (e.g., vaccination records, medical records) by receiving the pet's health information from one or more external services 150 (e.g., veterinarians, clinics, pet hospital, interactive chats, and the like). The diagnostic system 142 may store the pet's health information in the pet profile(s) 118. In an embodiment, the diagnostic system 142 may communicate the pet's health information using APIs 106.

The diagnostic system 142 may create personalized diagnostics 144 and/or a personalized wellness plan 146 based on the pet's health information. The personalized diagnostics 144 may include one or more diagnoses (e.g., ear infection, eye infection, and the like) of medical conditions for the pet. The personalized diagnostics 144 may be based on diagnoses and/or observations made by the external services 150. In some embodiments, the personalized diagnostics 144 may be based on diagnoses made by one or more machine learning models. The personalized wellness plan 146 may include one or more recommendations regarding eating events, exercise events, health checks and wellness visits, and the like, which may be based on the pet's health information. The personalized wellness plan 146 may be based on recommendations made by the external services 150. The personalized wellness plan 146 may be based on information included in the pet profile(s) 118. In some embodiments, the personalized wellness plan 146 may be based on one or more recommendations made by one or more machine learning models.

The diagnostic system 142 may facilitate the expert interactions 147 during which a pet owner interacts with an expert in various fields, such as a veterinarian, a veterinary technician, a pet behaviorist, a pet nutritionist, or the like. The expert may be associated with one of the external services 150, and may provide remote, online, and/or virtual services to conduct appointments, provide consultations, etc. with the pet and pet owner. Interaction with the expert may include, for example, an audio call, a video call, a text-based chat, or the like. In some embodiments, the expert may be a different entity than the pet's ordinary veterinarian. Thus, data generated from the expert interactions 147, such as one or more of a transcript, an audio recording, a video recording, one or more images, and/or notes, may be beneficial for future interactions with another one or more of the external services 150, such as the pet's ordinary veterinarian.

In-person veterinary appointments can be time-consuming and costly for pet owners, and may be uncomfortable for pets. Additionally, pet owners often are uncertain whether their pet's health and/or behavior warrants veterinarian attention. The expert interactions 147 provide pet owners an alternative option upon identifying a potential health and/or behavioral condition of their pet. For example, upon remotely assessing the pet's potential health and/or behavioral condition during the interaction, the experts may provide the pet owner advice as to whether and/or when to schedule a veterinary or other pet care related appointment. This may reduce the number of unnecessary appointments, as well as encourage more prompt veterinarian attention when the condition warrants it. As described herein, the expert interactions 147 are facilitated by the diagnostic system 142. However, in other examples, a separate system of the platform environment 100 may be dedicated to facilitating the expert interactions 147.

The health portal 148 may provide access to one or more parties who wish to retrieve the personalized diagnostics 144, personalized wellness plan 146, expert interactions 147, and/or the pet's health information from the pet profile(s) 118. The health portal 148 may be internal or external to the diagnostic system 142. Additionally, the health portal 148 may include a user interface. For example, a groomer may access the health portal 148 to retrieve the pet's vaccination records from diagnostic system 142.

The diagnostic system 142 may communicate with one or more of the external services 150, such as veterinarians, clinics, pet hospital, virtual experts, and the like. For example, one of the external services 150 (e.g., veterinarian) may send updated vaccine or medical records to the diagnostic system 142, where the diagnostic system 142 may then store such updated vaccine or medical records in the pet profile(s) 118. Additionally, for example, the diagnostic system 142 may update the personalized diagnostics 144 and/or the personalized wellness plan 146 based on the updated vaccine or medical records. In the case of virtual experts, the external services 150 may send data generated during remote, virtual, and/or online interactions with the virtual experts to diagnostic system 142. The diagnostic system 142 may then store such data, in the form of one or more of a transcript, an audio recording, a video recording, one or more images, and/or notes in the pet profile(s) 118.

In some embodiments, the diagnostic system 142 may include information to authenticate the pet. For example, social media websites frequently require that a user is authenticated in order to label the user as "verified" (e.g., a blue checkmark). The diagnostic system 142 may contain information corresponding to a physical examination of the pet. Such information may include authentication information of the pet. For example, the authentication information may include a confirmation of the pet's breed, gender, image, etc. Such authentication information may be used by a social media website to authenticate the pet as a "verified" user.

Homing System

The homing system 152 may match a future pet owner with a pet and provide additional support for the future pet owner. The homing system 152 may be an internal component or an external component of the platform 102, where the homing system 152 may communicate with the platform 102 via APIs 106.

The homing system 152 may match a future pet owner with a particular pet using a personalized matching module 154 and/or a search engine 156. The personalized matching module 154 may use user information (e.g., user location, user age, and the like) from the future pet owner (e.g., from the pet owner profile 120) to automatically search for one or more pets that are best suited for the future pet owner. In some embodiments, the personalized matching module 154 may use one or more machine learning models to determine the best pet matches for the future pet owner. The search engine 156 may allow the future pet owner to search for one or more pets. The search engine 156 may include different search filters (e.g., filtering by breed, age, size, weight, and the like), which may allow the user to filter the results of the one or more pets.

Both the personalized matching module 154 and/or the search engine 156 may retrieve results from one or more external services 162. The external services 162 may include one or more of: a pet adoption agency, a shelter, a pet breeder, and the like. When the personalized matching module 154 and/or the search engine 156 is performing a search for one or more pets, the personalized matching module 154 and/or the search engine 156 may send one or more requests to the external services 162 for available pets that fit one or more parameters contained in the one or more requests. Upon receiving the one or more requests, the external services 162 may search one or more databases for one or more matching pets. The external services 162 may send a response to the personalized matching module 154 and/or the search engine 156. The response may include the one or more matching pets. Alternatively, for example, if no matching pets were found, the response may include an indicator that no matching pets were found. In some embodiments, the homing system 152 may store the one or more matching pets in a database, such as an internal database or an external database (e.g., one of the database(s) 104).

The homing system 152 may display the one or more matching pets to the future pet owner, along with an option for the future pet owner to adopt and/or purchase the one or more matching pets. The homing system 152 may also facilitate the adoption and/or purchase of the one or more matching pets. In some embodiments, the homing system 152 may communicate with the external services 162 to facilitate the adoption and/or purchase of the one or more matching pets.

Once the future pet owner purchases and/or adopts the pet, the homing system 152 may store and/or manage the pet's adoption/registration record 160. In some embodiments, the homing system 152 may receive all (or part of) the pet's adoption/registration record 160 from the external services 162. In some embodiments, the homing system 152 may store the pet's adoption/registration record 160 in the pet profile(s) 118. Additionally, or alternatively, the homing system 152 may store the pet's adoption/registration record in the pet owner profile 120. In some embodiments, the homing system 152 may store the pet's adoption/registration record 160 in an internal or external database (e.g., one of the database(s) 104).

The homing system 152 may provide additional support for the future pet owner by providing personalized recommendations 158 to the pet owner. The personalized recommendations 158 may be based on characteristics of the pet that the future pet owner purchased and/or adopted. Example personalized recommendations 158 may include a recommended pet food, a recommended pet provider, recommended pet supplies, and the like. In some embodiments, the personalized recommendations 158 may be based on communications with one or more of the external services 162 and/or other systems associated with the platform 102. For example, the homing system 152 may communicate with the content management system 164 to receive personalized content 168, and then make personalized recommendations 158 based on the personalized content 168.

Content Management System

The content management system 164 may provide personalized content 168 to a user. The content management system 164 may be an internal component or an external component of platform 102, where the content management system 164 may communicate with the platform 102 via APIs 106.

The content management system 164 may retrieve the personalized content 168 and display such personalized content 168 to the user. The personalized content 168 may include at least one of: an article, a blog post, an online forum, an advertisement, and the like. The personalized content 168 may also include recommendations that are specific towards the pet and/or user. The recommendations may include food recommendations, activity recommendations, product recommendations, resource recommendations (e.g., books, articles, and the like), third party services recommendations (e.g., groomer, trainer, boarding), and the like. The personalized content 168 may be personalized based on the pet profile(s) 118 and/or the pet owner profile 120. The content management system 164 may display the personalized content 168 via a user interface of a user device. In some embodiments, the content management system 164 may retrieve the personalized content 168 from one or more external services 166. The external services 166 may include an electronic magazine, one or more databases, one or more social media posts, and the like. In some embodiments, the content management system 164 may retrieve the personalized content 168 from other sources, such as the database(s) 104, the cloud storage 114, and the personalized advertising system 108. In some embodiments, the content management system 164 may create personalized content 168 based on communications with the other external systems (e.g., wellness system 124, diagnostic system 142, homing system 152, genetics system 170, third party services system 182, etc.). For example, the content management system 164 may receive the personalized wellness plan 146 from diagnostic system 142. The personalized content 168 may then be based on (or include) information from the personalized wellness plan 146. Furthermore, the content management system 164 may receive data associated with the expert interactions 147 from diagnostic system 142. The personalized content 168 may then be based on (or include) information from the expert interactions 147, such as one or more of a transcript, an audio recording, a video recording, one or more images, and/or notes.

Genetics System

The genetics system 170 may analyze and/or monitor a pet's genetic data. The genetics system 170 may be an internal component or an external component of the platform 102, where the genetics system 170 may communicate with the platform 102 via APIs 106.

The genetics system 170 may include genetic data analysis 172, genetic data monitoring 174, and/or personalized recommendations 176. Additionally, the genetic data analysis 172 and/or the genetic data monitoring 174 may communicate with one or more external services 180 to assist with the analysis and/or the monitoring of the genetic data. The external services 180 may include a laboratory, a clinic, a veterinarian, and the like.

The genetic data analysis 172 may receive genetic data belonging to a pet. In some embodiments, the genetic data analysis 172 may receive the genetic data from a genetic data retrieval system 178. The genetic data retrieval system 178 may retrieve and store genetic data belonging to one or more pets. Additionally, the genetic data analysis may receive genetic data from the genetic data retrieval system 178, where the received genetic data is used in the analysis of the genetic data belonging to the pet. The genetic data analysis 172 may analyze the genetic data to determine abnormalities, potential genetic traits, familial relationships, and the like. In some embodiments, the genetic data analysis 172 may communicate with one or more of the external services 180 to assist with the analysis of the genetic data. For example, the genetic data analysis 172 may send genetic data information to a laboratory for the laboratory to perform the analysis of the genetic data.

The genetic data monitoring 174 may monitor the genetic data belonging to a pet to determine any changes in the genetic data. For example, the genetic data monitoring 174 may receive new genetic data and compare the new genetic data to previously stored genetic data. The comparing may lead the genetic data monitoring 174 to determine that there is an abnormality or an improvement in the genetic data. In some embodiments, the genetic data monitoring 174 may communicate with one or more of the external services 180, in order for the external services 180 to analyze the genetic data and determine if there are any changes.

The genetics system 170 may provide personalized recommendations 176 to the user. For example, the genetics system 170 may provide personalized recommendations 176 to the user via a user interface of a user device. In some embodiments, the personalized recommendations 176 may be based on the genetic data analysis 172 and/or the genetic data monitoring 174. The personalized recommendations 176 may include a pet food recommendation, an exercise recommendation, a pet item recommendation, health checks or wellness visits, and the like. In some embodiments, the personalized recommendations 176 may be based on communications with one or more of the external services 180 and/or other systems associated with the platform 102. For example, the genetics system 170 may communicate with the diagnostic system 142. The genetics system 170 may send a request to the diagnostic system 142 for a personalized wellness plan 146. The request may include, for example, the genetic data analysis 172 and/or the genetic data monitoring 174. The diagnostic system 142 may communicate the personalized wellness plan 146 to the genetics system 170, where the personalized wellness plan 146 may be based on the genetic data analysis 172 and/or the genetic data monitoring 174. The genetics system 170 may make personalized recommendations 176 to the user based on the personalized wellness plan 146.

In some embodiments, the genetics system 170 may include information to authenticate the pet. For example, social media websites frequently require that a user is authenticated in order to label the user as "verified" (e.g., a blue checkmark). The genetics system 170 may contain information corresponding to a physical examination of the pet. Such information may include authentication information of the pet. For example, the authentication information may include a confirmation of the pet's breed, gender, image, etc. Such authentication information may be used by a social media website to authenticate the pet as a "verified" user.

Third Party Services System

The third party services system 182 may allow a user to search for and reserve different external services 190, such as groomers, trainers, veterinarians, sitters, holistic care (e.g., nutritionist, naturopathic, or the like), and the like. The third party services system 182 may be an internal component or an external component of the platform 102, where the third party services system 182 may communicate with the platform 102 via APIs 106.

The third party services system 182 may include a search engine 184, a booking engine 186, and/or a management component 188.

The search engine 184 may allow the user, such as a pet owner, to search for one or more of the external services 190 to reserve for the user's pet. The search engine 184 may include filtering functionality to facilitate a fine-tuned search. The filtering functionality may include universal filtering and/or service specific filtering. For example, the universal filtering may include filtering the external services 190 by location, price range, and/or ratings. Additionally, for example, the service specific filtering may include filtering the external services 190 by breed specialty, health issues, and/or behavioral needs.

The booking engine 186 may allow the user to reserve the external services 190. For example, after using the search engine 184 to search for external services 190, the user may use the booking engine 186 to reserve a particular service of the external services 190. The booking engine 186 may present open dates and time slots, which may correspond to the selected external service 190. The user may then use the booking engine 186 to select a date and/or time from the displayed open dates and time slots. Upon the finalization of the booking, the user may receive an instant confirmation of the booking, such as via text or email. The user may also have the ability to instantly pay for the booked service. Alternatively, the user may be able to pay upon the finalization of the service. The user may be able to upload photos and include notes to the external service 190. For example, the user may upload dog photos to a groomer, or make a note that the user's dog has a limp.

The management component 188 may provide functionality to manage the different external services 190. For example, the management component 188 may provide the functionality for the external services 190 to register and/or be removed from the third party services system 182. The management component 188 may communicate with one or more databases (e.g., the database(s) 104) and/or cloud storage (e.g., the cloud storage 114) to store information (e.g., a name, a business identifier, a specialty, and the like) corresponding to the external services 190.

Exemplary Pet Owner Profile and Pet Profile(s)

Figure 2:
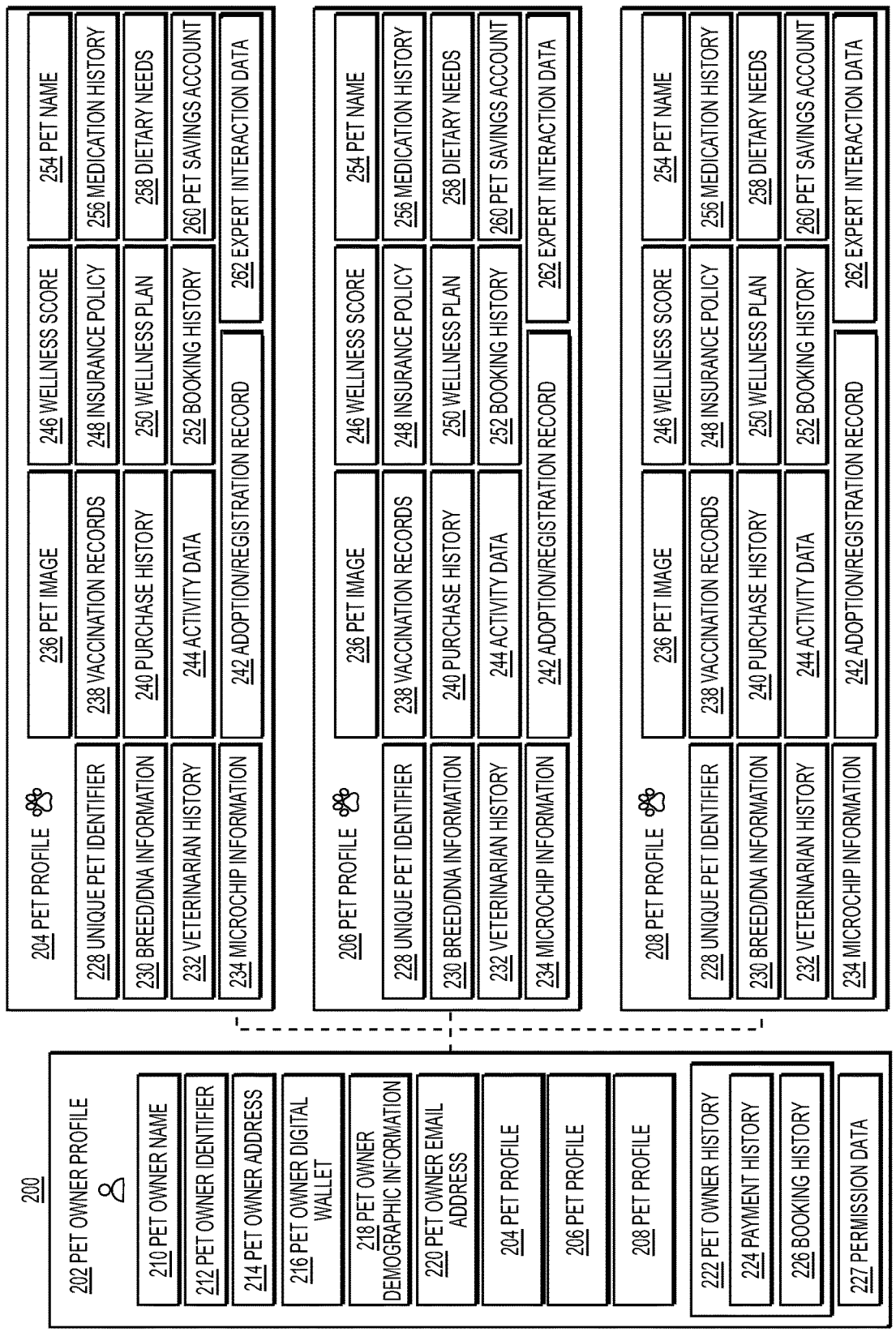
FIG. 2 depicts an exemplary environment of a pet owner profile and corresponding pet profiles, according to one or more embodiments.

FIG. 2 depicts an exemplary environment 200 of a pet owner profile 202 and corresponding pet profiles that may be utilized with the techniques presented herein. Notably, exemplary platform environment 200 may complement exemplary platform environment 100, with a pet owner profile 202 corresponding to the pet owner profile 120 of FIG. 1. Additionally, a pet profile 204, a pet profile 206, and/or a pet profile 208 may correspond to the pet profile(s) 118 of FIG. 1.

The pet owner profile 202 may include at least one of: a pet owner name 210, a pet owner identifier 212, a pet owner address 214, a pet owner digital wallet 216, pet owner demographic information 218, a pet owner email address 220, at least one pet profile (e.g., the pet profile 204, the pet profile 206, and/or the pet profile 208) and/or at least one identifier associated with the at least one pet profile, and/or a pet owner history 222. The pet owner name 210 may include a name of the pet owner. The pet owner identifier 212 may include a unique identifier that may be used to locate the pet owner profile 202. In some embodiments, the pet owner identifier 212 may allow for tracking of some or all of the user's activities. The pet owner address 214 may include a physical address of the pet owner. The pet owner digital wallet 216 may include payment information, such as credit card information, cryptocurrency information, and the like. The pet owner demographic information 218 may include a particular demographic of the pet owner. The pet owner email address 220 may include an email address of the pet owner. The pet owner profile may include at least one pet profile (e.g., the pet profile 204, the pet profile 206, and/or the pet profile 208). In some embodiments, in lieu of including an entirety of the at least one pet profile, the pet owner profile 202 may include at least one identifier associated with the at least one pet profile (e.g., a unique pet identifier 228). Each of the pet profiles may correspond to a pet that belongs to the pet owner. The number of pet profiles may be dynamic, where the pet profiles may adjust according to the number of pets that belong to the user.

The pet owner history 222 may include a payment history 224 and/or a booking history 226. The payment history 224 may include financial transactions of the pet owner. In some embodiments, the payment history 224 may correspond to activity of the pet owner digital wallet 216. In some embodiments, the payment history 224 may be tracked and analyzed to provide for targeted advertising (e.g., of personalized advertising system 108) and/or recommendations to the pet owner. The booking history 226 may include previous bookings of third party services that were made by the user. In some embodiments, the booking history 226 may be tracked and analyzed to provide for targeted advertising (e.g., of personalized advertising system 108) and/or recommendations to the pet owner.

The pet owner profile 202 may further include permission data 227 which allows the platform 102 to control which portions of data in the pet profiles 204, 206, and/or 208 each of the various systems (e.g., the content management system 164) of the environment 100 may access and/or modify. For example, permission data 227 may permit the content management system 164 to access activity data 244 and/or expert interaction data 262 of the pet profiles 204, 206, and/or 208, but may not permit the content management system 164 to access the pet savings account 260.

In some embodiments, the permission data 227 may be programmed or configured commensurate with the tasks each of the various systems of environment 100 performs. For example, the content management system 164 may have limited permission that does not allow access to information such as insurance policy 248, pet savings account 260, and other information not relevant to the functionality of content management system 164. Similarly, the third party services system 182 may have limited permission that does not allow access to information such as activity data 244 and other information not relevant to the functionality of third party services system 182.

In operation, the platform 102 may act as a gatekeeper of the data contained in the pet profiles 204, 206, and/or 208 by distributing one or more portions of the data in accordance with the permission data 227, where the distribution may be automatic and/or in response to a request from the pet owner and/or one or more of the systems associated with the platform 102. The permission data 227 may initially be provided with default settings intended to protect predetermined data within the pet profiles 204, 206, and/or 208 deemed to be private and/or sensitive (e.g., pet savings account 260). The pet owner may edit the permission data 227, for example via user interface 112, to replace the default settings and control access privileges for each of the different types of data contained in each of the pet profiles 204, 206, and/or 208.

The pet profiles 204, 206, and/or 208 may each correspond to a different pet that belongs to the pet owner of the pet owner profile 202. The pet owner may have more or less than three pets. The number of pet profiles may be dynamic, where the number of pet profiles corresponds to the number of pets that belong to the pet owner. In some embodiments, the pet owner may want only a subset of the pet owner's pets to have pet profiles.

The pet profiles 204, 206, and/or 208 may each include at least one of: a unique pet identifier 228, breed/DNA information 230, veterinarian history 232, microchip information 234, a pet image 236, vaccination records 238, a purchase history 240, an adoption/registration record 242, activity data 244, a wellness score 246, an insurance policy 248, a wellness plan 250, a booking history 252, a pet name 254, medication history 256, dietary needs 258, a pet savings account 260, and/or expert interaction data 262.

The unique pet identifier 228 may include a unique identifier that may be used to locate the corresponding pet profile (e.g., the pet profiles 204, 206, and/or 208). In some embodiments, the unique pet identifier 228 may allow for tracking of some or all of activities corresponding to the pet.

The pet image 236 may include a photograph, drawing, virtual presence, and/or avatar of the pet. The pet name 254 may include the name of the pet and/or any nicknames. The insurance policy 248 may include a pet insurance policy for the pet. The purchase history 240 may include purchases made for the pet. The pet savings account 260 may include a financial savings account for the pet. In some embodiments, the pet image 236, the pet name 254, the purchase history 240, pet savings account 260, and/or the insurance policy 248 may have been received from one or more of the external systems.

The breed/DNA information 230 may correspond to the breed and/or DNA information of the pet. In some embodiments, the breed/DNA information 230 may have been received from one or more of the external systems. For example, the breed/DNA information 230 may have been received from genetics system 170.

The veterinarian history 232 may include the details of the pet's visit(s) to a veterinarian. The veterinarian history 232 may also include notes from the vet and/or possible diagnoses and treatments. The vaccination records 238 may include one or more vaccination records of vaccinations administered to the pet. The medication history 256 may include details of the medications that the pet currently takes and/or has taken in the past. The dietary needs 258 may include information regarding food that the pet should eat and/or food that the pet should avoid. The wellness plan 250 may correspond to a wellness plan for the pet. In some embodiments, the wellness plan 250 may have been determined based on the personalized wellness plan 146. In some embodiments, the veterinarian history 232, vaccination records 238, dietary needs 258, wellness plan 250, and/or the medication history 256 may have been received from one or more of the external systems. For example, the veterinarian history 232, vaccination records 238, dietary needs 258, wellness plan 250, and/or the medication history 256 may have been received from diagnostic system 142.

The microchip information 234 may include a microchip number of the pet. For example, the microchip may have been inserted into the pet to track the pet. The adoption/registration record 242 may include documentation of the adoption or purchase of the pet. In some embodiments, the microchip information 234 and/or adoption/registration record 242 may have been received from one or more of the external systems. For example, the microchip information 234 and/or adoption/registration record 242 may have been received from homing system 152.

The activity data 244 may include data corresponding to physical activities, sleep activities, and/or food activities of the pet. For example, the activity data may be collected by a smart collar 130, a smart bed 132, a smart food dispenser 134, a smart litter box 136, a smart camera 138, and/or the other sensors 140 for collecting a digital image of a pet's life. The wellness score 246 may include data corresponding to a wellness score produced by wellness index scoring system 128. In some embodiments, the activity data 244 and/or the wellness score 246 may have been received from one or more of the external systems. For example, the activity data 244 and/or the wellness score 246 may have been received from the wellness system 124.

The booking history 252 may include data corresponding to one or more bookings of a third party service (e.g., groomer, trainer, and the like). In some embodiments, the booking history 252 may have been received from one or more of the external systems. For example, the booking history 252 may have been received from the third party services system 182.

The expert interaction data 262 may include data generated, gathered, or otherwise obtained from the expert interactions 147. In some embodiments, the expert interaction data 262 may include a transcript, an audio recording, a video recording, one or more images, and/or notes generated during an interaction between the pet owner and an expert (e.g. an expert associated with one of the external services 150).

First Exemplary Method

Figure 3A:
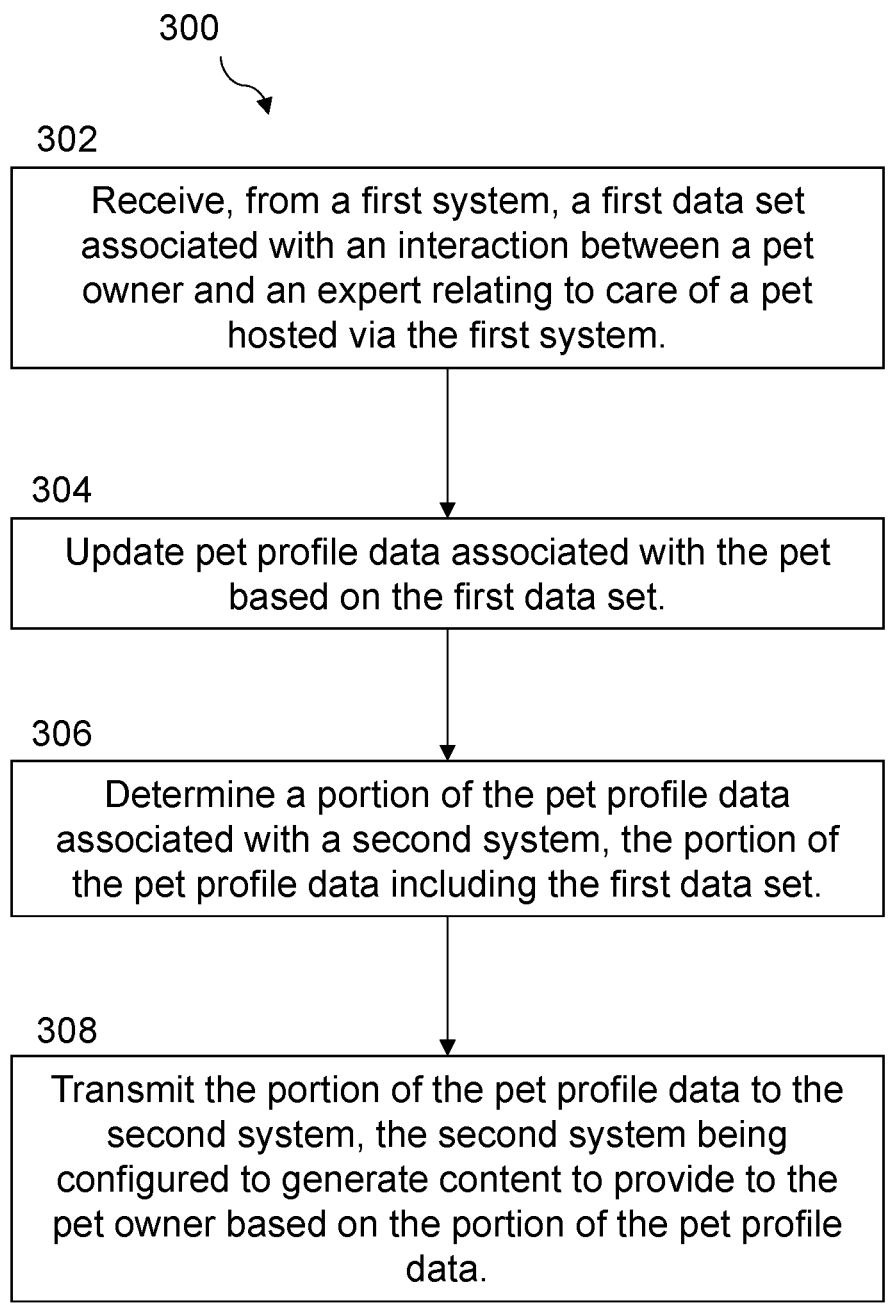
FIG. 3A depicts a flowchart of an exemplary method, according to one or more embodiments.

FIG. 3A illustrates an exemplary method 300 performed by at least one processor, according to one or more embodiments. Notably, the method 300 may be performed by one or more processors of a device/server that is in communication with one or more user devices and other external system(s) via a network. That is, each of step 302-308 of the method 300 may be performed by at least one processor, such as at least one processor associated with the platform 102.

The method 300 may include, at step 302, receiving a first data set from a first system associated with an interaction between a pet owner and an expert relating to care of a pet associated with pet profile 204, 206, or 208. For simplicity in explaining the method 300, the following description of steps 302-308 will assume that the pet is associated with the pet profile 204. The interaction may be an expert interaction 147 hosted via the first system. The first system may include, for example, the diagnostic system 142. The first data set may include expert interaction data (e.g., from the expert interaction 147), such as one or more of a transcript, an audio recording, a video recording, one or more images, and notes. The expert may be, for example, a veterinarian, a veterinary technician, a pet behaviorist, a pet nutritionist, or the like associated with the external services 150. In some embodiments, the first data set may include information disclosed to or provided by the expert during and/or after the interaction. In some embodiments, the interaction may include an interactive chat (e.g., an audio call, a video call, text chat, or the like).

With continued reference to FIG. 3A, the method 300 may further include, at step 304, updating pet profile data associated with the pet based on the first data set. Pet profile data may include, for example, any of the information/data 228-262 contained in the pet profile 204. For example, based on the first data set including information from the expert interaction 147, step 304 may include updating the expert interaction data 262 to reflect the first data set.

With continued reference to FIG. 3A, the method 300 may further include, at step 306, determining a portion of the pet profile data associated with a second system. The second system may be the content management system 164. The portion of the pet profile data determined to be associated with the second system includes at least the first data set, and may further include additional data from the pet profile 204 that is relevant to the performance of a task by the second system. That is, the portion of the pet profile data associated with the second system may be a subset of the pet profile data that the second system requires to perform a task. For example, the portion of the pet profile data may include at least the expert interaction data 262 of the pet profile 204 that was updated to reflect the first data set at step 304. Additionally or alternatively, the same or different portions of the pet profile data including the first data set may be provided to one or more of the other systems of the environment 100, such as the diagnostic system 142, the homing system 152, the content management system 164, the genetics system 170, and/or the third party services system 182. For example, by providing the first data set to the diagnostic system 142, the expert interaction data 262 may be accessible for viewing by one of the external services 150 (e.g., a veterinarian if a subsequent in-person appointment is scheduled for the pet).

In some embodiments, the method 300 may further include, prior to step 306, receiving a request by the second system to access the pet profile data. The request may be for certain data that the second system requires to perform the task. For example, for the content management system 164, the request may be for at least the expert interaction data 262 for use in generating personalized content for the pet owner that is relevant to the information provided by the expert during the expert interaction 147. Additionally, the request may also be for other data, such as the activity data 244, the wellness plan 250, and/or other data from the pet profile 204 to further tailor the content.

In some embodiments, the request may be initiated independently by the second system. For example, the second system may be configured to intermittently query data for the purpose of updating records, in which case the second system may automatically initiate the request at predetermined time intervals. In some embodiments, the platform 102 and/or the first system may trigger the second system to initiate the request. For example, the platform 102 may alert the second system upon receiving the first data set, which prompts the second system to initiate the request. In some embodiments, the request may come from a source other than the second system, such as from the pet owner. That is, the pet owner may input a command into the platform 102 via the user interface 112 requesting data to be shared with the second system.

In some embodiments, the platform 102 may automatically perform step 306, i.e. without the second system explicitly sending a request, upon completion of step 304.

With continued reference to FIG. 3A, the method 300 may further include, at step 308, transmitting the portion of the pet profile data to the second system. The second system is configured to generate content to provide to the pet owner based on the portion of the pet profile data. In some embodiments, the content may be articles, videos, product advertisements, or other media content tailored to the pet.

Although FIG. 3A shows example blocks of exemplary method 300, in some implementations, the exemplary method 300 may include additional blocks, fewer blocks, different blocks, or differently arranged blocks than those depicted in FIG. 3A. Additionally, or alternatively, two or more of the blocks of the exemplary method 300 may be performed in parallel, where context would allow.

As is apparent from the foregoing description, the method 300 may be implemented to facilitate data aggregation and distribution across many/all of the various systems of environment 100. In particular embodiments of the method 300, the first system and the second system may be various systems from FIG. 1, and the first data set may include various information obtained from the first system and/or components thereof. In some embodiments, the first system and the second system may be different systems of environment 100—e.g., the first system may be the diagnostic system 142 and the second system maybe the content management system 164. In some embodiments, the first system and the second system may be the same system—e.g., the first system and the second system may both be the diagnostic system 142.

In an exemplary embodiment of the method 300, the first system may include the diagnostic system 142, and the first data set may include expert interaction data disclosed to or provided by an expert during an interactive session (e.g., the expert interactions 147) via external services 150. Thus, at step 304 of method 300, the expert interaction data 262 is updated, and, at step 306, the portion of the pet profile data associated with the second system includes the expert interaction data 262. The second system may include the content management system 164, so the expert interaction data 262 may be transmitted to the content management system 164 at step 308. The content management system 164 may be configured to utilize the expert interaction data 262, particularly the information from the first data set, to perform the task of generating personalized content 168 (e.g., an article, a product advertisement, and/or other media) to the pet owner based on the portion of the pet profile data. The content management system 164 may generate the personalized content 168 further based on other pet profile data received, such as the activity data 244 provided by the wellness system 124, among other systems. In some embodiments, the method 300 may further include receiving the personalized content. Thus, method 300 may automatically provide relevant content to the pet owner based on the interactive chat between the pet owner and a care provider.

Additionally, the diagnostic system 142 may be configured to provide access to the expert interaction data 262, including at least the information from the first data set, to one or more of the external services 150, such as a veterinarian or other care provider prior to a veterinary or other care-related visit. Thus, the method 300 may take an onus off of the pet owner to record and/or remember the expert interaction data 262 that may be pertinent to diagnosis and/or treatment of the pet during a subsequent veterinary visit. Further, the method 300 may efficiently provide information to the veterinarian that the pet owner would not have known to be relevant if not for engagement with the expert during the interaction.

In some embodiments, the method 300 may include receiving, from the second system, an indication that the pet owner has been interacting with content (e.g., an article) related to a care topic via the second system. The indication may be received by the platform 102 prior to step 302. The method 300 may further include, based on the indication, generating a user interface (e.g., a user interface 510 of FIG. 5) prompting the pet owner to initiate the interaction between the pet owner and the expert. Generating the user interface may be performed by the platform 102 prior to step 302. The expert may have expertise associated with the care topic.

In some embodiments, expert data associated with a plurality of experts may be stored in a database (e.g. database 104). Platform 102 may select an expert for participation in the interaction based on the expert data including subject matter expertise, availability, client feedback, user preferences, familiarity with the pet, and/or the like. In some embodiment, the platform 102 may perform a lookup function to select an expert, such as an expert most suited to the pet based on the expert data and the reason (e.g., the pet condition/behavior) for the interaction. In some embodiments, the platform 102 may present the user with a list of qualified, available experts from which the user may select the expert.

In some embodiments, the method 300 may include receiving, from one or more other systems of the environment 100, an indication that the pet is experiencing a condition based on data collected by the one or more other systems. For example, the wellness system 124, the diagnostic system 142, and/or the genetics system 170 may transmit the indication based on data collected by one or more of these systems. The condition may include for example, excessive scratching by the pet detected by the smart collar 130 and/or the smart camera 138. The indication may be received by the platform 102 prior to step 302. The method 300 may further include, based on the indication, generating a user interface (e.g., the user interface 510 of FIG. 5) prompting the pet owner to initiate the interaction between the pet owner and the expert. The expert may have expertise associated with the condition. Generating the user interface may be performed by the platform 102 prior to step 302.

The embodiments of the method 300 described herein are a non-exhaustive list of those that can performed in accordance with the present disclosure. For example, various systems of the environment 100 may exchange data as described herein such that the portion of the pet profile data determined at step 306 includes information received from, for example, a device (e.g., the smart collar 130) of the first system worn by the pet; an appliance (e.g., the smart bed 132, the smart food dispenser 134, or the smart litter box 136) of the first system used by the pet; a camera (e.g., the smart camera 138) of the first system; the personalized content 168 of the first system; the genetic data monitoring 174 of the first system; and genetic data analysis 172 of the first system.

Second Exemplary Method

Figure 3B:
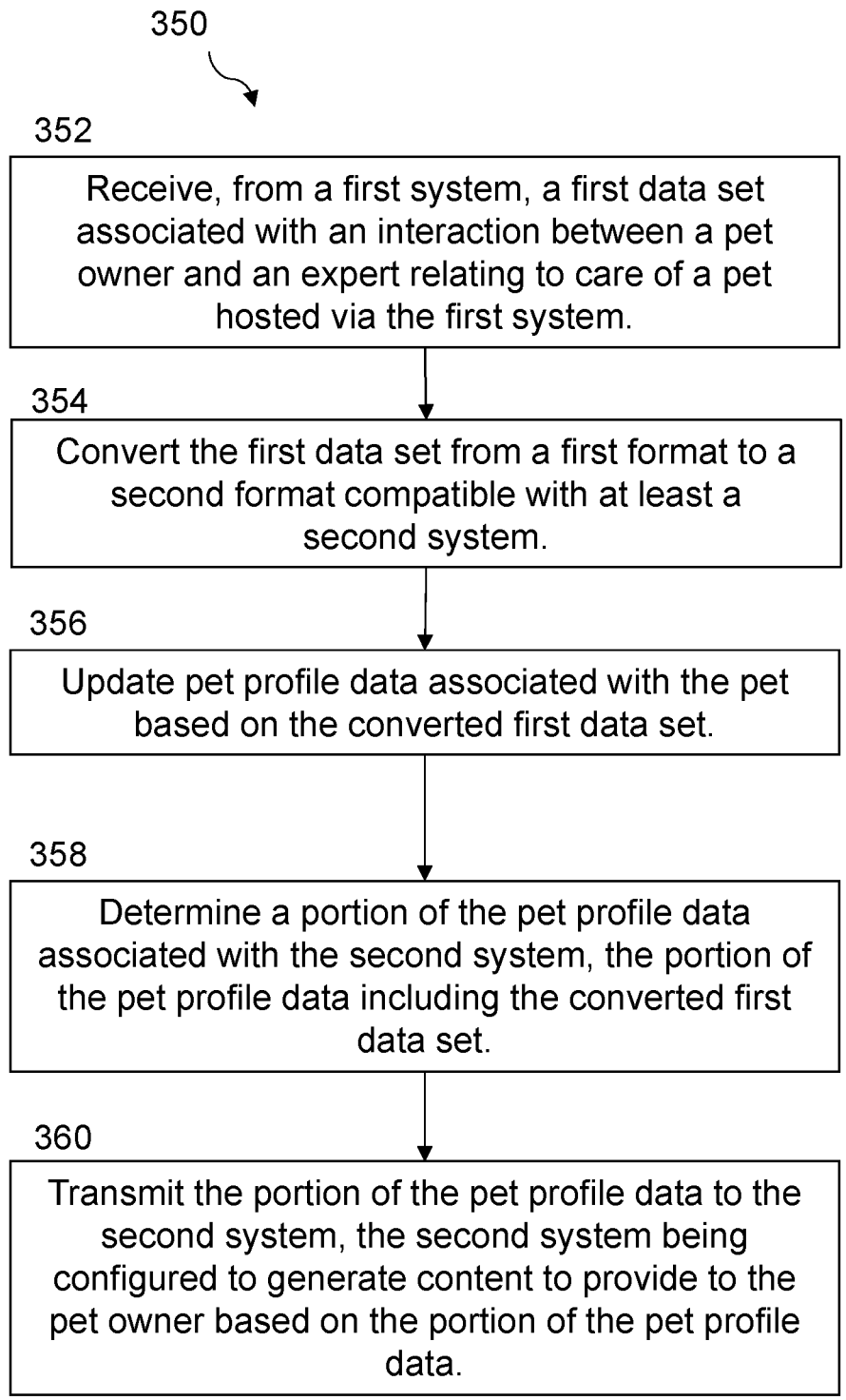
FIG. 3B depicts a flowchart of an exemplary method, according to one or more embodiments.

FIG. 3B illustrates an exemplary method 350 performed by at least one processor, according to one or more embodiments. The method 350 may be similar to the method 300, but includes a step to convert data from one system into a format usable by another system, thus allowing otherwise incompatible systems to communicate. Notably, the method 350 may be performed by one or more processors of a device/server that is in communication with one or more user devices and other external system(s) via a network. That is, each of steps 352-360 of the method 350 may be performed by at least one processor, such as at least one processor associated with the platform 102.

The method 350 may include steps corresponding to steps 302-308 of the method 300. For example, the method 350 may include, at step 352, receiving a first data set from a first system associated with an interaction between a pet owner and an expert relating to care of a pet hosted via the first system, which may be similar to step 302 of the method 300. In the method 350, the first data set is received in a first format compatible with the first system. That is, the first data set is provided in a format in which it is used by the first system.

With continued reference to FIG. 3B, the method 350 may further include, at step 354, converting the first data set from the first format to a second format. The second format may be compatible with a plurality of systems, including at least the second system. Thus, where the first format of data is incompatible with the second system (and therefore could not be used by the second system), the second format is compatible with the second system.

With continued reference to FIG. 3B, the method 350 may further include, at step 356, updating pet profile data associated with the pet based on the converted first data set. Step 356 may substantially correspond to step 304 of the method 300, except that the pet profile data is updated based on the converted first data set in the method 350, rather than the raw first data set in the method 300.

With continued reference to FIG. 3B, the method 350 may further include, at step 358, determining a portion of the pet profile data associated with the second system. The portion of the pet profile data includes the converted first data set. Step 358 may substantially correspond to step 306 of the method 300. The method 350 may further include, at step 360, transmitting the portion of the pet profile data to the second system. The second system may be configured to generate content to provide to the pet owner based on the portion of the pet profile data. Step 360 may substantially correspond to step 308 of the method 300.

Although FIG. 3B shows example blocks of exemplary method 350, in some implementations, the exemplary method 300 may include additional blocks, fewer blocks, different blocks, or differently arranged blocks than those depicted in FIG. 3B. Additionally, or alternatively, two or more of the blocks of the exemplary method 350 may be performed in parallel, where context would allow.

As is apparent from the foregoing description, the method 350 may be implemented to facilitate data aggregation and distribution across many/all of the various systems of environment 100. In particular, method 350 may be implemented in substantially the same manner as the various exemplary embodiments discussed herein in connection with method 300.

Third Exemplary Method

Figure 4:
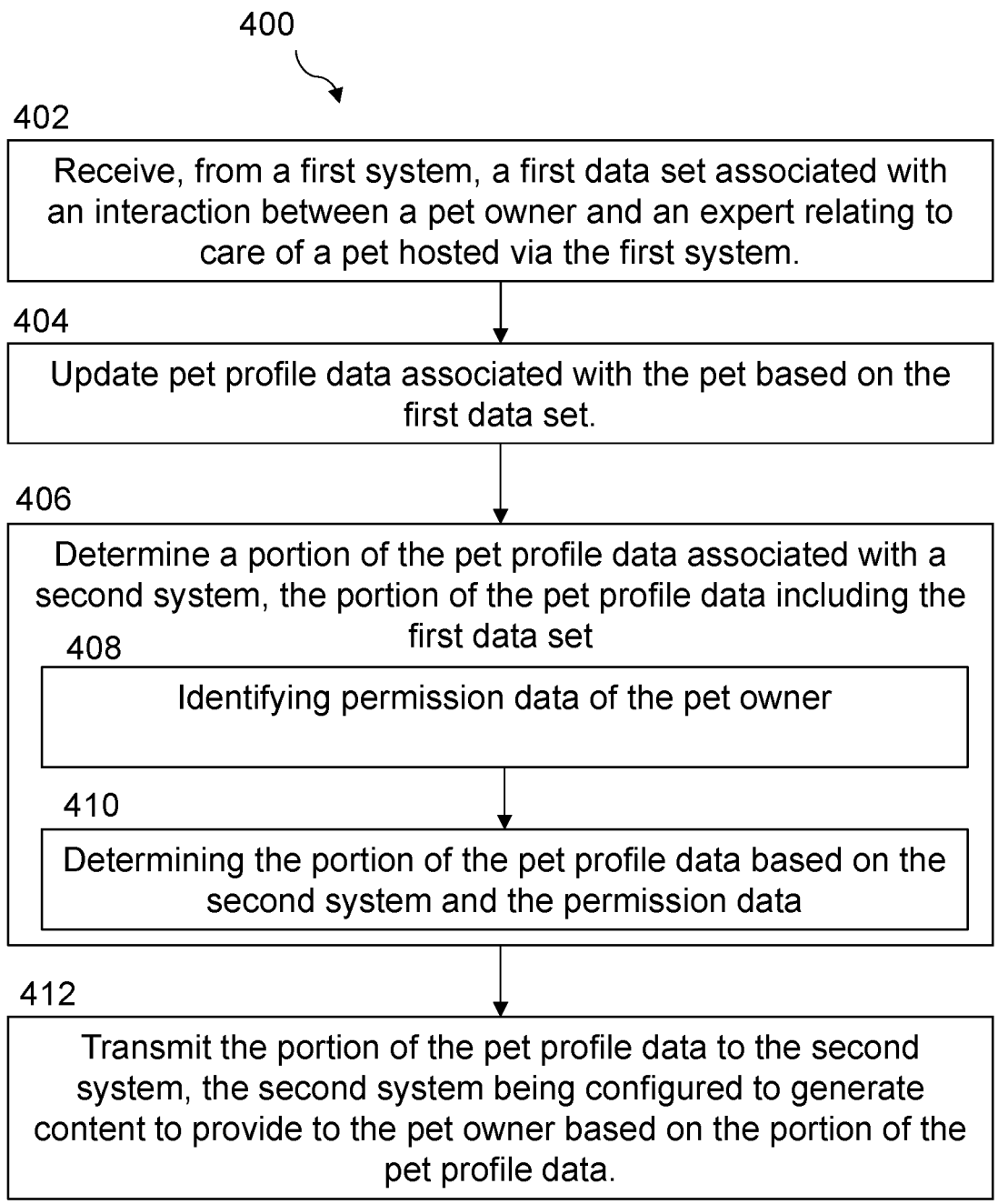
FIG. 4 depicts a flowchart of an exemplary method, according to one or more embodiments.

FIG. 4 illustrates an exemplary method 400 performed by at least one processor, according to one or more embodiments. Notably, the method 400 may be performed by one or more processors of a device/server that is in communication with one or more user devices and other external system(s) via a network. That is, each of step 402-412 of the method 400 may be performed by at least one processor, such as at least one processor associated with the platform 102.

Method 400 may include steps corresponding to steps 302-308 of the method 300. For example, the method 400 may include, at step 402, receiving a first data set from a first system associated with an interaction between a pet owner and an expert relating to care of a pet hosted via the first system, which may be similar to step 302 of the method 300. In some examples, the first data set may include an identifier of the pet owner (and/or an identifier of the pet from which the identifier of the pet owner may be determined). The identifier of the pet owner may correspond to the pet owner identifier 212 of the pet owner profile 202. Due to the inclusion of the identifier of the pet owner (and/or identifier of the pet) in the first data set, the platform 102 may identify the pet owner associated with the first data set—i.e., the owner associated with the interaction.

The method 400 may further include, at step 404, updating pet profile data associated with the pet based on the first data set, which may be substantially identical to step 304 of the method 300.

Referring still to FIG. 4, the method 400 may further include, at step 406, determining a portion of the pet profile data associated with the second system, which may correspond to step 306 of the method 300. In some examples, step 406 may be performed automatically based on the updating of the pet profile data at step 404. In other examples, step 406 may be performed in response to a request from the second system for data and/or a request from the pet owner to provide data to the second system. When the request is received from the second system and/or pet owner, the identifier of the pet owner may be included in the request.

In the method 400, step 406 may include substep 408 of identifying permission data 227 of the pet owner. In some example, the permission data 227 may be identified using the identifier of the pet owner included in the first data set and/or provided in the request from the second system and/or pet owner. The platform 102 may determine the pet owner by matching the identifier of the pet owner to the pet owner identifier 212 of the pet owner profile 202, and then identify the permission data 227 associated with that pet owner profile 202. Step 406 may further include substep 410 of determining the portion of the pet profile data based on the second system and the permission data 227. In particular, the platform 102 utilizes permission data 227 to determine which data of the pet profile 204 that the second system is permitted to access. Thus, data which permission data 227 prohibits the second system from accessing is not included in the portion of the pet profile data associated with the second system. For example, if the second system is the content management system 164, and the permission data 227 indicates that the content management system 164 does not have access authority to the vaccination records 238, then the portion of the profile data will not include the vaccination records 238.

Referring still to FIG. 4, the method 400 may further include, at step 412, transmitting the portion of the pet profile data to the second system, which may be substantially identical to step 308 of the method 300.

Although FIG. 4 shows example blocks of exemplary method 400, in some implementations, the exemplary method 400 may include additional blocks, fewer blocks, different blocks, or differently arranged blocks than those depicted in FIG. 4. Additionally, or alternatively, two or more of the blocks of the exemplary method 400 may be performed in parallel, where context would allow.

As is apparent from the foregoing description, the method 400 may be implemented to facilitate data aggregation and distribution across many/all of the various systems of environment 100. In particular, method 400 may be implemented in substantially the same manner as the various exemplary embodiments discussed herein in connection with method 300.

Exemplary Implementation

Figure 5:
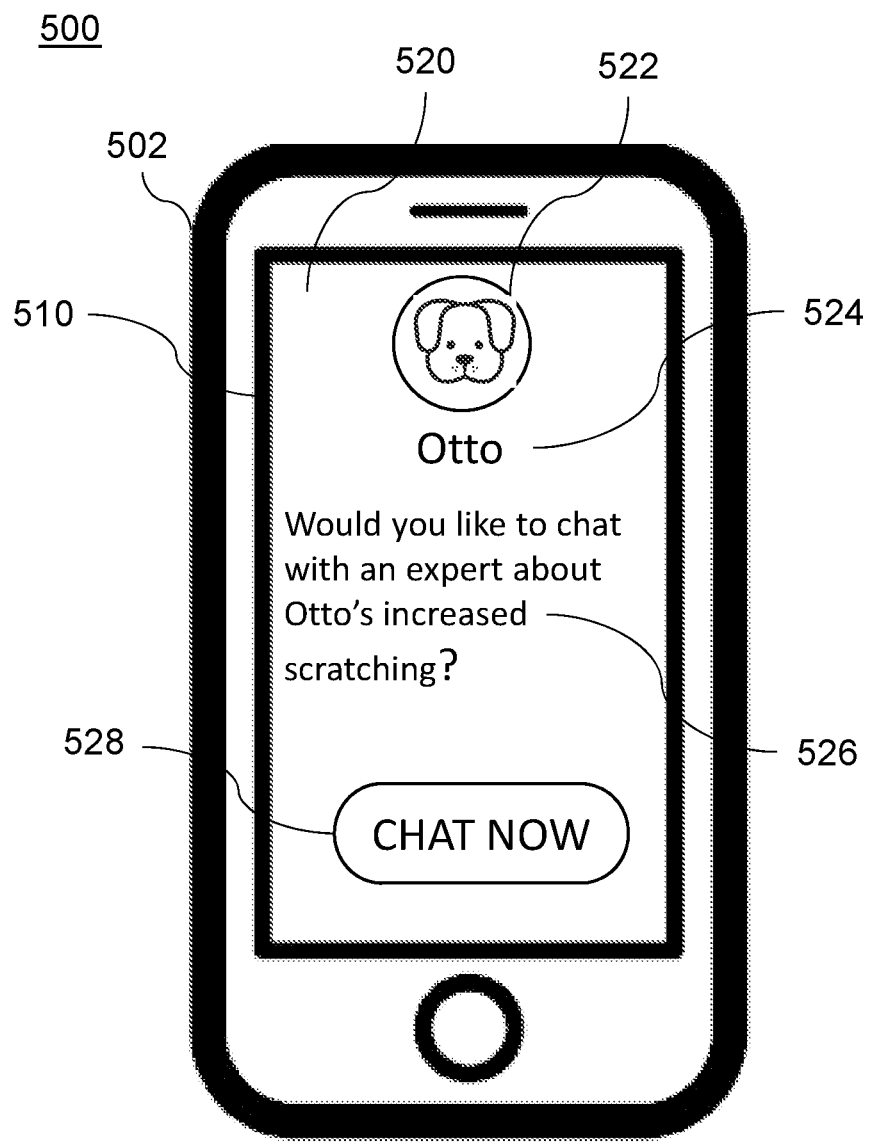
FIG. 5 depicts an exemplary implementation on a user device, according to one or more embodiments.

FIG. 5 depicts an exemplary implementation 500 on a user device that may be utilized with the techniques presented herein. The implementation includes a user device 502, which is illustrated in the form of a smart device such as a smart phone or tablet. User device 502 includes a user interface 510 (e.g., user interface 112 of FIG. 1) through which a user (e.g., a pet owner) may interact with platform 102. User interface may display various prompts, messages, or the like, to the user according to the various techniques described herein.

As illustrated in FIG. 5, the user interface 112 may display a prompt 520. The prompt 520 may be generated and displayed by at least one processor in response to various systems of environment 100 of FIG. 1 receiving and/or generating data. For example, the prompt 520 shown in FIG. 5 may be generated in response to the wellness system 124 detecting that the pet (e.g., a pet associated with the profile 204) is exhibiting behavior such as unusual and/or excessive scratching. Particularly, the smart collar 130 and/or smart camera 138 may detect the unusual and/or excessive scratching, and the wellness system 124 may automatically provide updated activity data 244 to the platform 102 for storage in association with the pet profile 204 to reflect this behavior. In response to the activity data 244 being updated, the platform 102 may generate and display the prompt 520 on the user interface 510. In some examples, the platform 102 may display prompt 520 on the user interface 510 upon a user's next access of the platform 102. In other examples, the platform 102 may also generate and transmit a notification or alert, such as a push notification, electronic message, and/or text message, to the user to prompt access of the platform 102.

The prompt 520 may include a photograph or avatar 522 of the pet (e.g., the pet image 236 from the pet profile 204) and the pet's name 524 so that the user is informed which pet is the subject of the prompt 520. The prompt 520 may further include a message 526 indicating the behavior and asking the user whether the user would like to take a course of action, such as chatting with an appropriate expert. In the illustrated embodiment, the message 526 is a text message stating "Would you like to chat with an expert about Otto's increased scratching?". In some embodiments, the message 526 may further include one or more images, videos, or the like to convey the subject behavior or condition to the user. The prompt 520 may further include one or more selectable inputs 528 (e.g., one or more buttons) that allow the user to proceed with one or more courses of action. In the illustrated embodiment, the selectable input 528 includes a button captioned "CHAT NOW".

The user may select (e.g., touch or click) the selectable input 528 to be connected to an expert (e.g., an expert associated with one of the external services 150) to conduct an interactive session (e.g., one of the expert interactions 147). Data associated with the interactive session may be compiled, for example, by the diagnostic system 142 and provided to the platform 102 for updating the expert interaction data 262 associated with the pet profile 204. The expert interaction data 262 may then be utilized by the platform 102 as described herein, such as during performance of the method 300, 350, or 400 in order to generate content (e.g. notes to provide to veterinarian during an in-person veterinary visit and/or to tailor or personalize content provided to the user).

In other embodiments, the prompt 520 may be automatically generated and displayed based on content that the pet owner is viewing and/or interacting with. For example, the content management system 164 may detect that the pet owner has searched for and/or is interacting with articles associated with a particular health and/or behavioral condition. In response, the content management system 164 may transmit a signal to the platform 102 to generate the prompt 520 asking the pet owner if would like to engage in an expert interaction to discuss the health and/or behavioral condition.

In some embodiments, another system of the environment 100 (e.g., the diagnostic system 142, the homing system 152, the genetics system 170, and/or the third party services system 182) may receive data or detect occurrences, behaviors, conditions, etc. that cause the platform to automatically generate the prompt 520.

Exemplary Platform Flow

Figure 6:
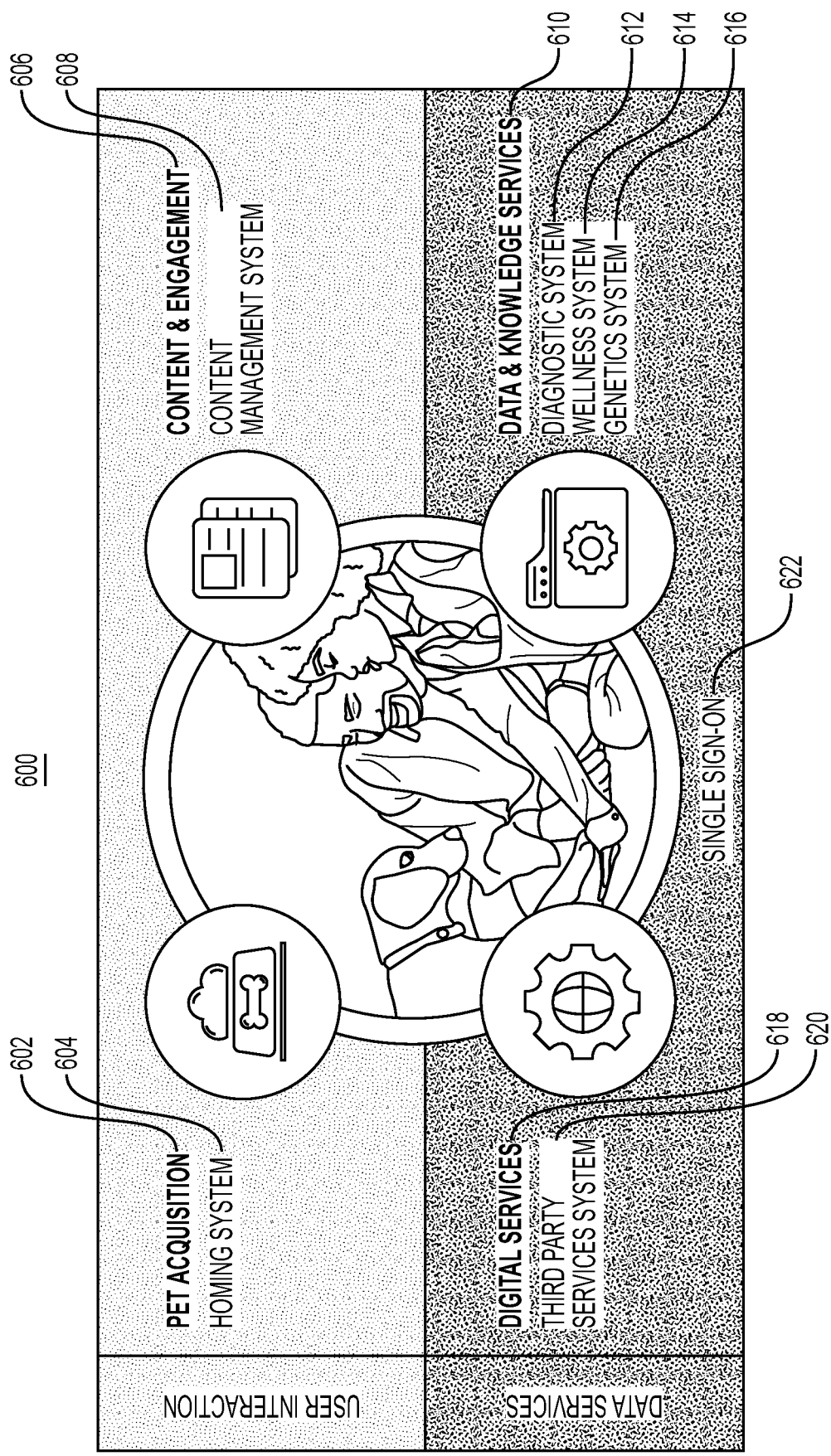
FIG. 6 depicts an exemplary platform flow, according to one or more embodiments.

FIG. 6 depicts an exemplary platform flow 600 that may be utilized with the techniques presented herein. Notably, the platform flow 600 may be performed by one or more processors of a server that is in communication with one or more user devices and other external system(s) via a network. However, it should be noted that platform flow 600 may be performed by any one or more of the server, one or more user devices, or other external systems.

The platform flow 600 may begin with a pet acquisition process 602, where the pet acquisition process 602 may utilize a homing system 604 (e.g., homing system 152). For example, the pet acquisition process 602 may utilize the homing system 604 in order to facilitate a user adopting and/or purchasing a pet.

After a user acquires the pet, the platform flow 600 may continue with providing content and engagement 606 to the user. For example, content and engagement 606 may utilize a content management system 608 (e.g., content management system 164) to provide personalized content (e.g., newsletters, advertisements) to the user.

The platform flow 600 may continue with providing data and knowledge services 610 to the user. For example, data and knowledge services 610 may utilize a diagnostic system 612 (e.g., diagnostic system 142), a wellness system 614 (e.g., wellness system 124), and/or a genetics system 616 (e.g., genetics system 170) to provide precision care to the user. Particularly, the data and knowledge services 610 may utilize data from expert interactions (e.g., expert interactions 147) to generate content in response to user requests for expert interactions, or in response to various systems (e.g., the diagnostic system 612, the wellness system 614, and/or the genetics system 616) automatically initiating or prompting an expert interaction based on data received by that system.

The platform flow 600 may continue with providing digital services 618 to the user. For example, digital services 618 may utilize a third party services system 620 (e.g., third party services system 182) to assist the user in searching for, and reserving, services for the user's pet.

In some embodiments, the user may be able to engage in all or some of the platform flow 600 by utilizing a single sign-on 622 (e.g., single sign-on 116). For example, the single sign-on 622 may allow for some or all of the user's activity in the platform flow 600 to be associated with the user and/or the user's pet.

Exemplary Environment

Figure 7:
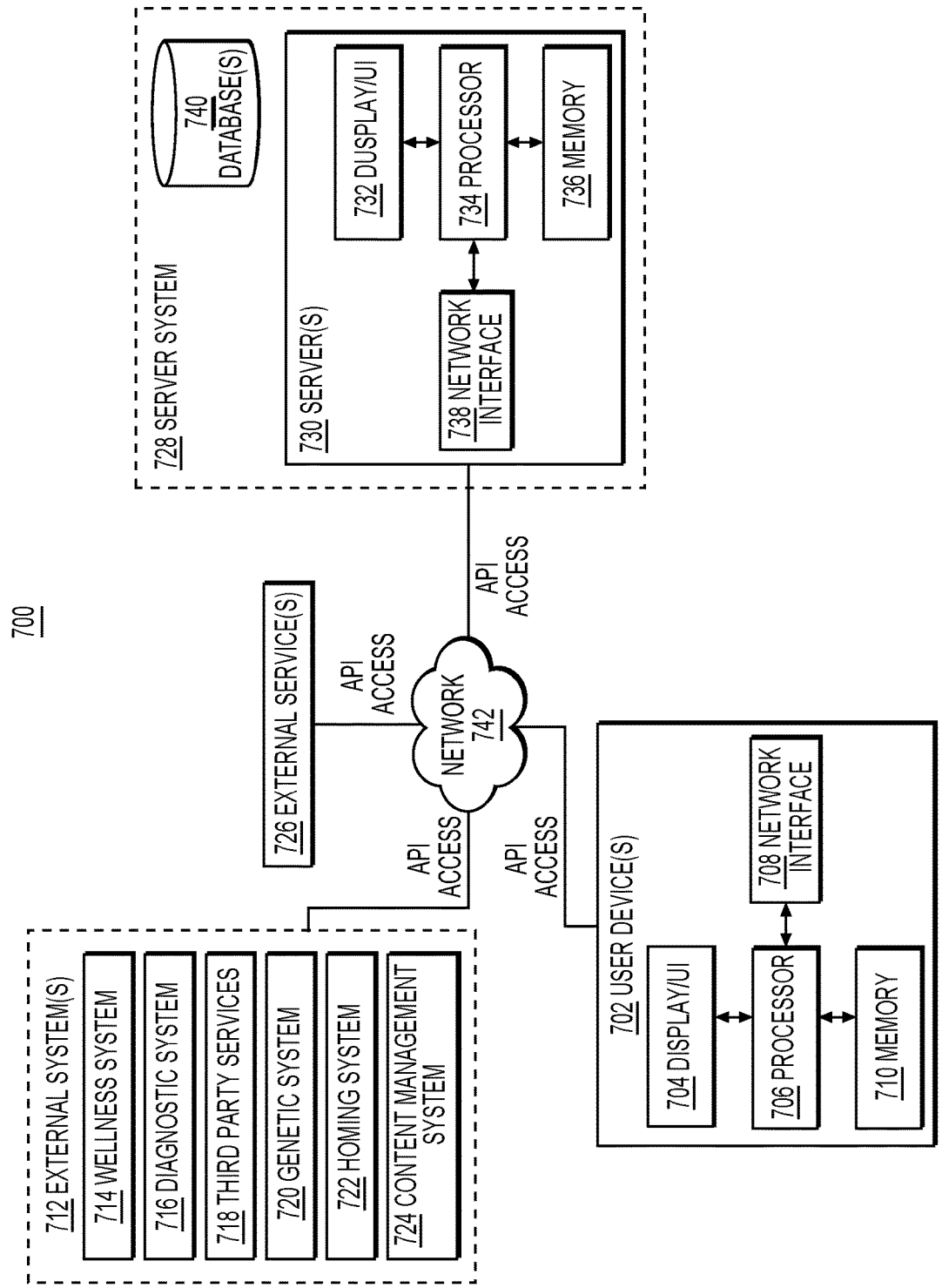
FIG. 7 depicts an exemplary environment that may be utilized with techniques presented herein, according to one or more embodiments.

FIG. 7 depicts an exemplary environment 700 that may be utilized with the techniques presented herein (e.g., methods 300, 350, and 400 and/or implementation 500). One or more user device(s) 702, one or more external service(s) 726, and one or more server system(s) 728 may communicate across a network 742. As will be discussed in further detail below, one or more server system(s) 728 may communicate with one or more of the other components of the environment 700 across network 742. The one or more user device(s) 702 may be associated with a user, e.g., a user associated with at least one pet.

In some embodiments, the components of the environment 700 are associated with a common entity, e.g., a veterinarian, clinic, animal specialist, research center, or the like. In some embodiments, one or more of the components of the environment is associated with a different entity than another. The systems and devices of the environment 700 may communicate in any arrangement. As will be discussed herein, systems and/or devices of the environment 700 may communicate in order to receive, send, and/or store data.

The user device 702 may be configured to enable the user to access and/or interact with other systems in the environment 700. For example, the user device 702 may be a computer system such as, for example, a desktop computer, a mobile device, a tablet, etc. In some embodiments, the user device 702 may include one or more electronic application(s), e.g., a program, plugin, browser extension, etc., installed on a memory of the user device 702.

The user device 702 may include a display/user interface (UI) 704, a processor 706, a memory 710, and/or a network interface 708. The user device 702 may execute, by the processor 706, an operating system (O/S) and at least one electronic application (each stored in memory 710). The electronic application may be a desktop program, a browser program, a web client, or a mobile application program (which may also be a browser program in a mobile O/S), an applicant specific program, system control software, system monitoring software, software development tools, or the like. For example, environment 700 may extend information on a web client that may be accessed through a web browser. In some embodiments, the electronic application(s) may be associated with one or more of the other components in the environment 700. The application may manage the memory 710, such as a database, to transmit streaming data to network 742. The display/UI 704 may be a touch screen or a display with other input systems (e.g., mouse, keyboard, etc.) so that the user(s) may interact with the application and/or the O/S. The network interface 708 may be a TCP/IP network interface for, e.g., Ethernet or wireless communications with the network 742. The processor 706, while executing the application, may generate data and/or receive user inputs from the display/UI 704 and/or receive/transmit messages to the server system 728, and may further perform one or more operations prior to providing an output to the network 742.

External system(s) 712 may be, for example, one or more systems that collect, manage, and/or store data corresponding to one or more pets and/or one or more pet owners. The one or more external systems may include at least one of a wellness system 714, a diagnostic system 716, a third party services system 718, a genetics system 720, a homing system 722, and/or a content management system 724. External system(s) 712 may be in communication with other device(s) or system(s) in the environment 700 over the one or more networks 742. For example, external system(s) 712 may communicate with the server system 728 via API (application programming interface) access over the one or more networks 742, and also communicate with the user device(s) 702 via web browser access over the one or more networks 742.

External service(s) 726 may be, for example, one or more third party and/or auxiliary systems that integrate and/or communicate with the server system 728 in performing various document information extraction tasks. External service(s) 726 may be in communication with other device(s) or system(s) in the environment 700 over the one or more networks 742. For example, external service(s) 726 may communicate with the server system 728 via API access over the one or more networks 742, and also communicate with the user device(s) 702 via web browser access over the one or more networks 742.

In various embodiments, the network 742 may be a wide area network ("WAN"), a local area network ("LAN"), a personal area network ("PAN"), or the like. In some embodiments, network 742 may include the Internet, and information and data provided between various systems occurs online. "Online" may mean connecting to or accessing source data or information from a location remote from other devices or networks coupled to the Internet. Alternatively, "online" may refer to connecting or accessing a network (wired or wireless) via a mobile communications network or device. The Internet is a worldwide system of computer networks-a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

The server system 728 may include an electronic data system, e.g., a computer-readable memory such as a hard drive, flash drive, disk, etc. In some embodiments, the server system 728 includes and/or interacts with an application programming interface for exchanging data to other systems, e.g., one or more of the other components of the environment.

The server system 728 may include a database(s) 740 and server(s) 730. The server system 728 may be a computer, system of computers (e.g., rack server(s)), and/or or a cloud service computer system. The server system may store or have access to database(s) 740 (e.g., hosted on a third party server or in memory 736). The server(s) may include a display/UI 732, a processor 734, a memory 736, and/or a network interface 738. The display/UI 732 may be a touch screen or a display with other input systems (e.g., mouse, keyboard, etc.) for an operator of the server(s) 730 to control the functions of the server(s) 730. The server system 728 may execute, by the processor 734, an operating system (O/S) and at least one instance of a servlet program (each stored in memory 736).

Although depicted as separate components in FIG. 7, it should be understood that a component or portion of a component in the environment 700 may, in some embodiments, be integrated with or incorporated into one or more other components. For example, a portion of the display/UI 732 may be integrated into the user device 702 or the like. In some embodiments, operations or aspects of one or more of the components discussed above may be distributed amongst one or more other components. Any suitable arrangement and/or integration of the various systems and devices of the environment 700 may be used.

In general, any process or operation discussed in this disclosure that is understood to be computer-implementable, such as the processes illustrated in FIGS. 3-5, may be performed by one or more processors of a computer system, such any of the systems or devices in the environment 700 of FIG. 7, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices in FIG. 7. One or more processors of a computer system may be included in a single computing device or distributed among a plurality of computing devices. A memory of the computer system may include the respective memory of each computing device of the plurality of computing devices.

Exemplary Device

Figure 8:
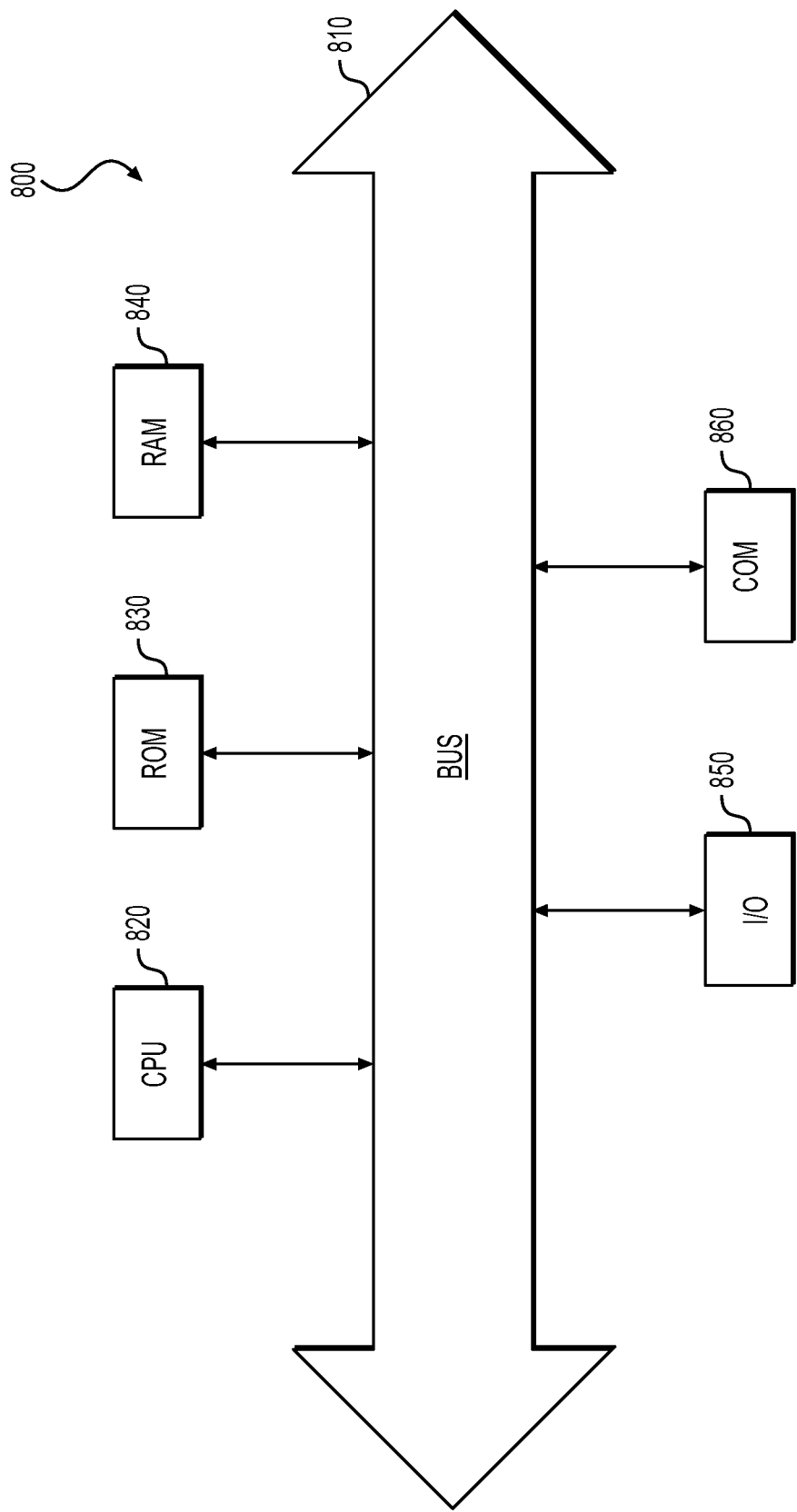
FIG. 8 depicts an example of a computing device that may execute the techniques described herein, according to one or more embodiments.

FIG. 8 is a simplified functional block diagram of a computer that may be configured as a device 800 for executing the environments and/or the methods of FIGS. 1-6, according to exemplary embodiments of the present disclosure. For example, device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multi-processor system, such system operating alone, or in a cluster of computing devices operating in a cluster or server farm. CPU 820 may be connected to a data communication infrastructure 810, for example, a bus, message queue, network, or multi-core message-passing scheme.

Device 800 also may include a main memory 840, for example, random access memory (RAM), and also may include a secondary memory 830. Secondary memory 830, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include other similar means for allowing computer programs or other instructions to be loaded into device 800. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical, or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 800 also may include input and output ports 850 to connect with input and output devices such as keyboards, mice, touchscreens, monitors, displays, readable media (e.g., barcode or QR code) scanner, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

A computer system, such as a system or device implementing a process or operation in the examples above, may include one or more computing devices. One or more processors of a computer system may be included in a single computing device or distributed among a plurality of computing devices. A memory of the computer system may include the respective memory of each computing device of the plurality of computing devices.

A computer may be configured as a device for executing the exemplary embodiments of the present disclosure. For example, the computer may be configured according to exemplary embodiments of this disclosure. In various embodiments, any of the systems herein may be a computer including, for example, a data communication interface for packet data communication. The computer also may include a central processing unit ("CPU"), in the form of one or more processors, for executing program instructions. The computer may include an internal communication bus, and a storage unit (such as ROM, HDD, SDD, etc.) that may store data on a computer readable medium, although the computer may receive programming and data via network communications. The computer may also have a memory (such as RAM) storing instructions for executing techniques presented herein, although the instructions may be stored temporarily or permanently within other modules of computer (e.g., processor and/or computer readable medium). The computer also may include input and output ports and/or a display to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Exemplary Application

Figure 9:
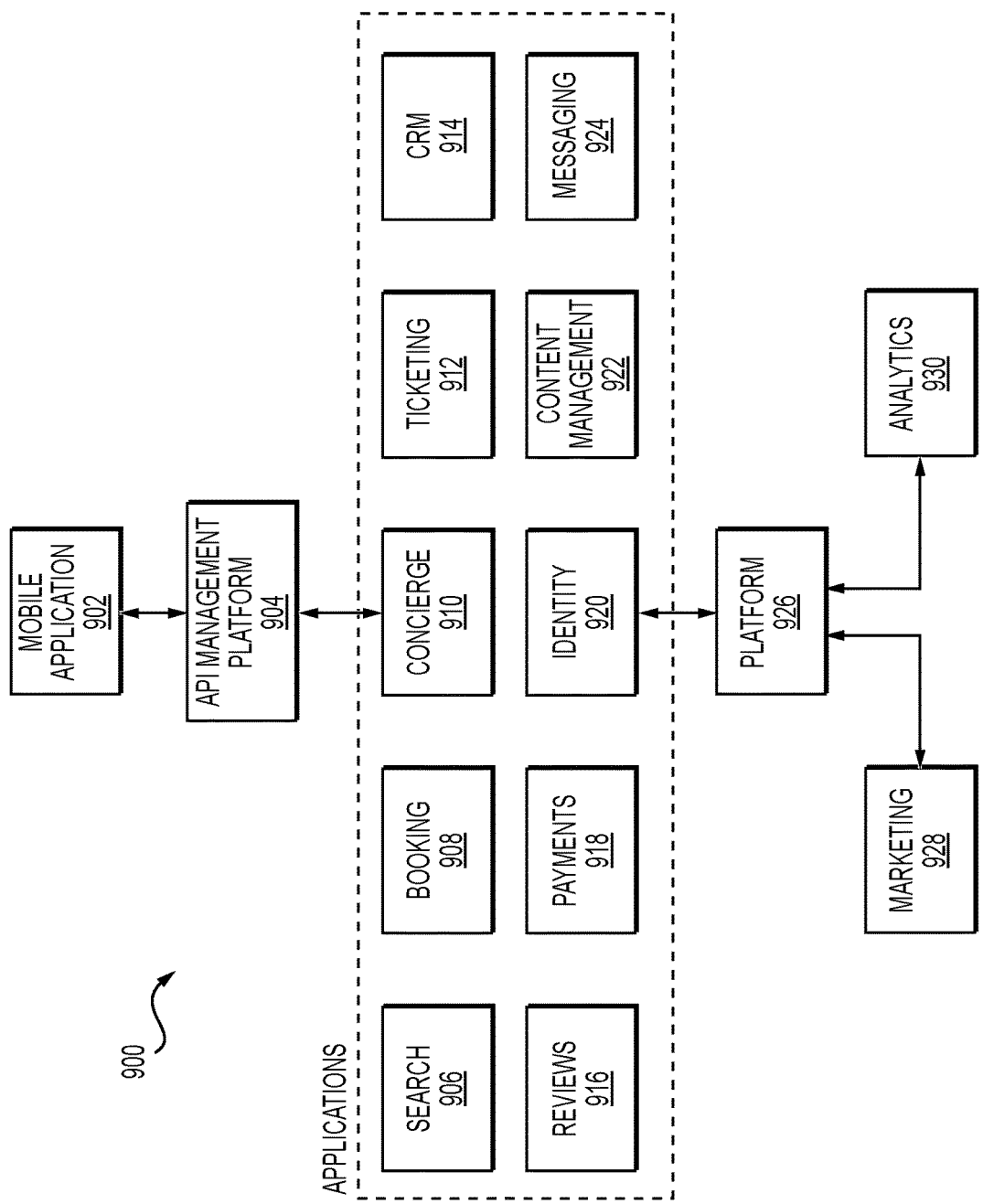
FIG. 9 depicts an exemplary system that may be utilized with techniques presented herein, according to one or more embodiments.

As shown in FIG. 9, a system 900 may include a mobile application 902, an API management platform 904, a search application 906, a booking application 908, a concierge application 910, a ticketing application 912, a customer relationship management (CRM) application 914, a reviews application 916, a payments application 918, an identity application 920, a content management application 922, a messaging application 924, a platform 926, a marketing application 928, and an analytics application 930. The system 900 may include any other number of applications. One or more components of the system 900 may correspond to one or more components of the exemplary environment 100 and/or the exemplary environment 200.

The mobile application 902 may be configured to permit a pet owner to communicate with various experts (e.g., veterinarians, nutritionists, trainers, etc.) related to care of the pet, and view content (e.g., articles, blogs, instructions, etc.) related to the pet. The mobile application 902 may attract and engage pet owners with compelling features, collect pet data to power the features, and utilize the pet data for other product features. The mobile application 902 may be associated with a particular pet owner identifier. The pet owner identifier may be associated with a parent profile and one or more pet profiles corresponding to pets of the owner. The mobile application 902 may provide various services to the user, such as a hotel concierge, a booking concierge, passport, café access, travel, veterinarian check-in, milestone reminders, insights, health score, ask-a-vet, caretaker roles, instant share, NoseID®, vaccine reminders, product recommendation, local alerts, wellness recommendation, lost pet, community board, document scanner, product scanner, personalized content, nutrition recommendation, or the like.

The API management platform 904 may be configured to permit the mobile application 902 to communicate with the search application 906, the booking application 908, the concierge application 910, the ticketing application 912, the CRM application 914, the reviews application 916, the payments application 918, the identity application 920, the content management application 922, the messaging application 924, the platform 926, the marketing application 928, and the analytics application 930.

The search application 906 may be configured to permit the mobile application 902 to search for various external services, experts, content, destinations, products, or the like. The booking application 908 may be configured to permit the mobile application 902 to book various services, appointments, or the like. The concierge application 910 may be configured to permit the mobile application 902 to book a concierge for a destination, hotel, or the like. The ticketing application 912 may be configured to permit the mobile application 902 to acquire various tickets, such as tickets to events, locations, or the like. The CRM application 914 may be configured to permit the mobile application 902 to track communications with various external services, experts, etc. The reviews application 916 may be configured to permit the mobile application 902 to provide reviews, such as reviews for services, experts, locations, events, products, food, or the like. The payments application 918 may be configured to permit the mobile application 902 to provide payments to external services, experts, stores, restaurants, sellers, or the like. The identity application 920 may be configured to permit the mobile application 902 to authenticate the pet owner, secure login information for the mobile application 902, or the like. The content management application 922 may be configured to permit the mobile application 902 to be updated, generated, or the like. The messaging application 924 may be configured to permit the mobile application 902 to communicate using various communication methods, such as phone call, short message service (SMS), multimedia messaging service (MMS), or the like. The platform 926 may be configured to store, collect, generate, etc., information associated with the pet and/or the pet owner. The marketing application 928 may be configured to permit the mobile application 902 to receive content that is tailored to the pet owner. The analytics application 930 may be configured to permit the mobile application 902 to generate analytics.

Figure 10:
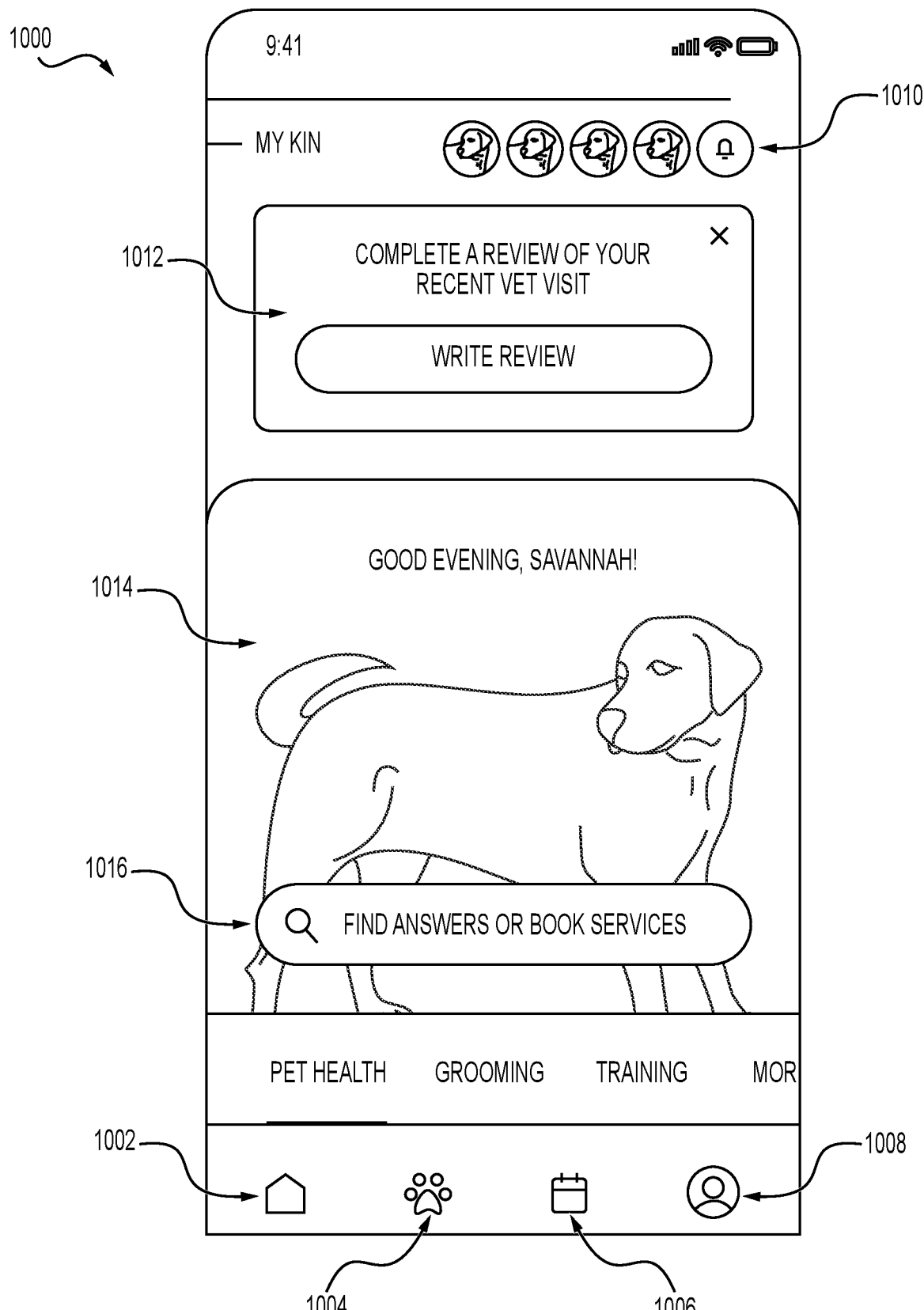
FIG. 10 depicts an exemplary home screen of a mobile application, according to one or more embodiments.

FIG. 10 is a diagram 1000 of a home screen of the mobile application 902. As shown in FIG. 10, the home screen may include a bottom navigation structure including a set of icons. For example, the home screen may include a home icon 1002, a pet icon 1004, an appointment icon 1006, and a profile icon 1008.

The home icon 1002, when interacted with, may cause the mobile application 902 to navigate to the home screen. The home screen may display a notifications icon 1010, content 1014, a search field 1016, or the like. The notifications icon 1010, when interacted with, may cause the mobile application 902 to display notifications, reminders, a to-do list, etc. The content 1014 may include articles, advertisements, product reviews, instructions, guidebooks, or the like. The content 1014 may be tailored to the user profile, the pet profile, interactions with external services and experts, browsing history, or the like. The home screen may include a set of tabs to navigate through respective content. For example, the home screen may display a "pet health" tab that displays content related to pet health, a "grooming" tab that displays content related to grooming, a "training" tab that displays content related to training, or the like. The search field 1016 may permit the user to enter search prompts to search for content, services, experts, or the like. The search field 1016 may display an "ask and expert" prompt that permits the user to submit a query to an expert. The home screen may display a best match screen for finding an expert. For example, the best match screen may include a reason for care, care filters, results (e.g., a map view, a list view, or the like), or the like.

The pet icon 1004, when interacted with, may cause the mobile application 902 to navigate to a set of pet profiles. A pet profile may include a photo of the pet, a name of the pet, an about section of the pet, parents of the pet, documents (e.g., vaccine records, photos, or the like) of the pet, a viewable and/or shareable pet identifier of the pet, or the like. The pet profile may link to appointment history of the pet.

The appointment icon 1006, when interacted with, may cause the mobile application 902 to navigate to a set of appointment screens. The appointment screens may include an appointment preparation screen, a pre-appointment check-in screen, a provider review screen, an appointment history screen, a request to book screen, a booking concierge screen, or the like. The appointment preparation screen may display appointment details, a to-do list, articles, or the like. The appointment preparation screen may link to a change or cancel appointment function and/or may link to the pre-appointment check-in screen. The pre-appointment check-in screen may display an introduction, a mood and wellness check, appointment notes, health history (e.g., vaccination records, microchip records, or the like), a completion confirmation, or the like. The pre-appointment check-in screen may link to the appointment preparation screen. The provider review screen may display a review rating, private feedback, a public review, a review submissions, or the like. The provider review screen may link to a provider profile and/or a user profile. The appointment history screen may display a pet associated with the appointment, an appointment type, a time and date of the appointment, a provider for the appointment, appointment notes, or the like. The appointment history screen may link to a pet profile, related articles, a book another appointment function, or the like. The request to book screen may display an appointment type, a time and date selection, a confirm request function, a request submitted confirmation, or the like. The request to book screen may link to related articles. The booking concierge screen may display information associated with a booking concierge.

The profile icon 1008, when interacted with, may cause the mobile application 902 to navigate to a user profile. The user profile may include a profile photo, a name, an email, a password, settings and preferences, permissions, or the like. The user profile may link to an invitation function for inviting family, friends, etc.

Figure 11A:
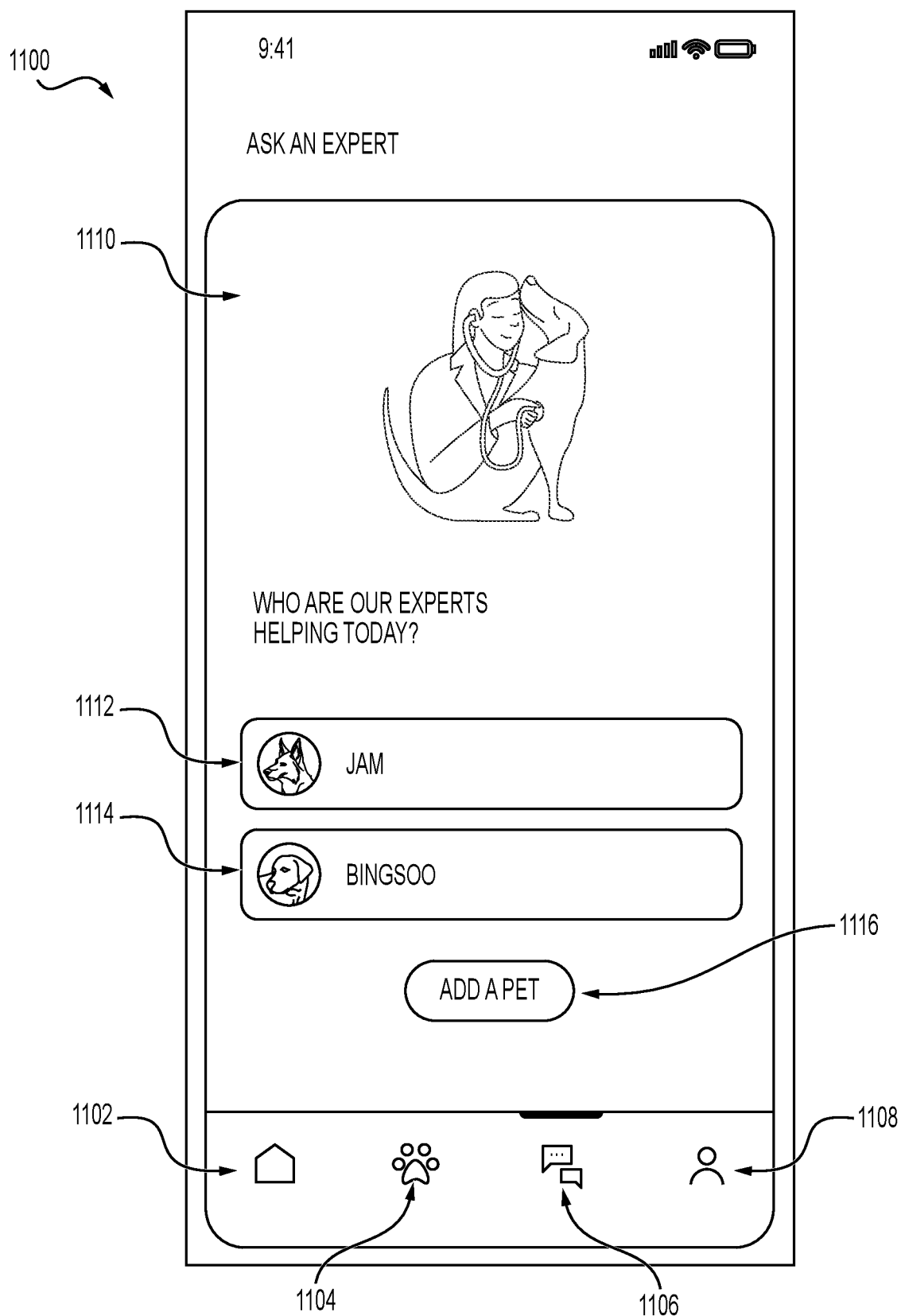
FIGS. 11A-11F depict diagrams of an example mobile application, according to one or more embodiments.

FIGS. 11A-11F are diagrams 1100 of the mobile application 902. As shown in FIG. 11A, the mobile application 902 may display a home icon 1102, a pet icon 1104, a chat icon 1106, and a profile icon 1108. The home icon 1102, the pet icon 1104, and the profile icon 1108 may be similar to the icons described above in connection with FIG. 10. The chat icon 1106, when interacted with, may cause the mobile application 902 to navigate to a set of expert chat screens.

The set of expert chat screens may include a pet selection screen 1110 that displays a set of pets associated with the expert chat. For example, the pet selection screen 1110 may display a first pet icon 1112 associated with a first pet of the user and a second pet icon 1114 associated with a second pet of the user. Further, the pet selection screen 1110 may display an add a pet icon 1116 that permits the user to add a different pet. The user may select a particular pet icon to select a pet to be the subject of the expert chat.

Figure 11B:
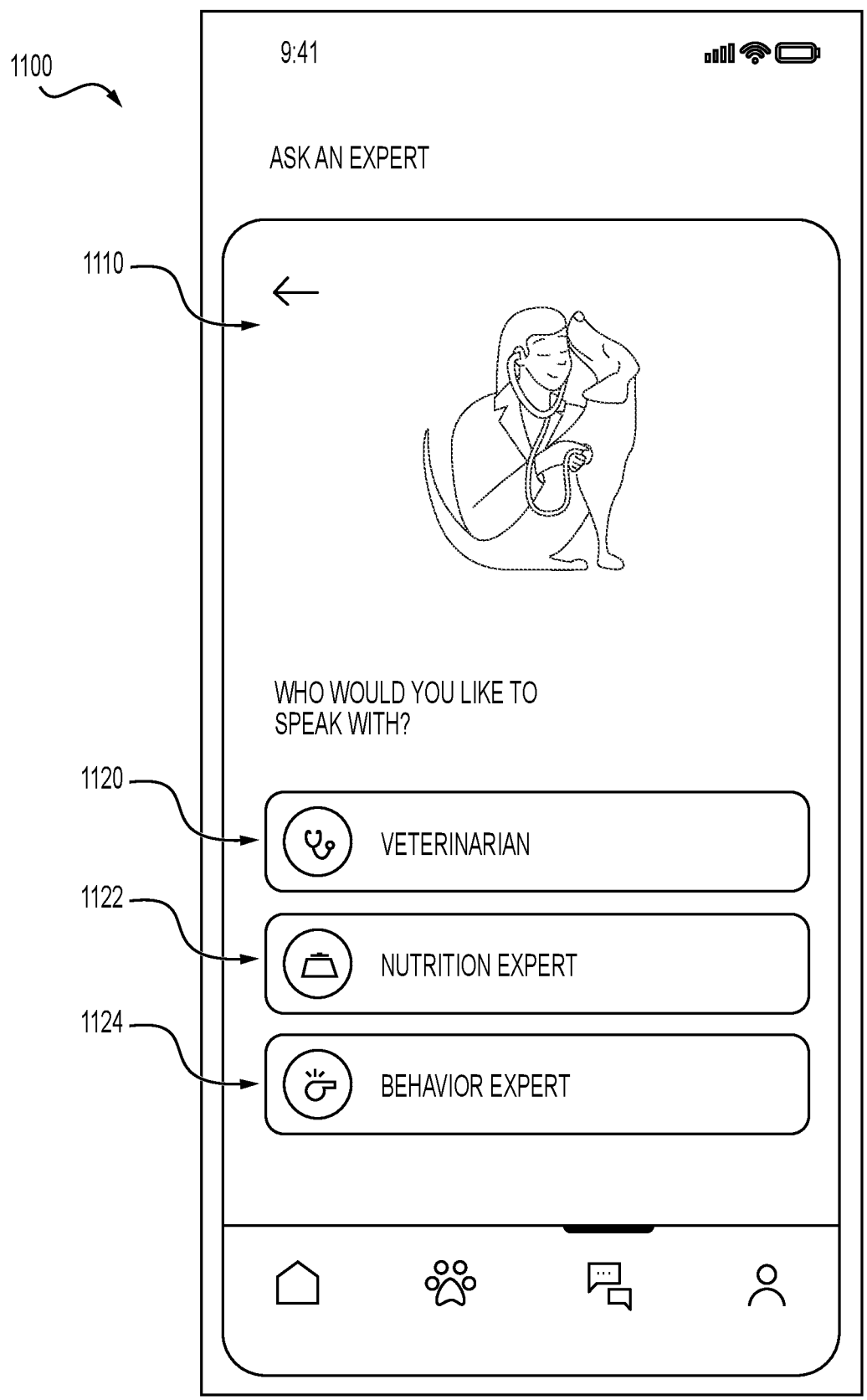

As shown in FIG. 11B, the set of expert chat screens may include an expert type selection screen 1118. The expert type selection screen 1118 may display a set of types of experts associated with the expert chat. For example, the expert type selection screen 1118 may display a first expert type icon 1120 associated with a first type of expert, a second expert type icon 1122 associated with a second type of expert, a third expert type icon 1124 associated with a third type of expert, etc. The user may select a particular expert type icon to select a particular type of expert associated with the expert chat.

Figure 11C:
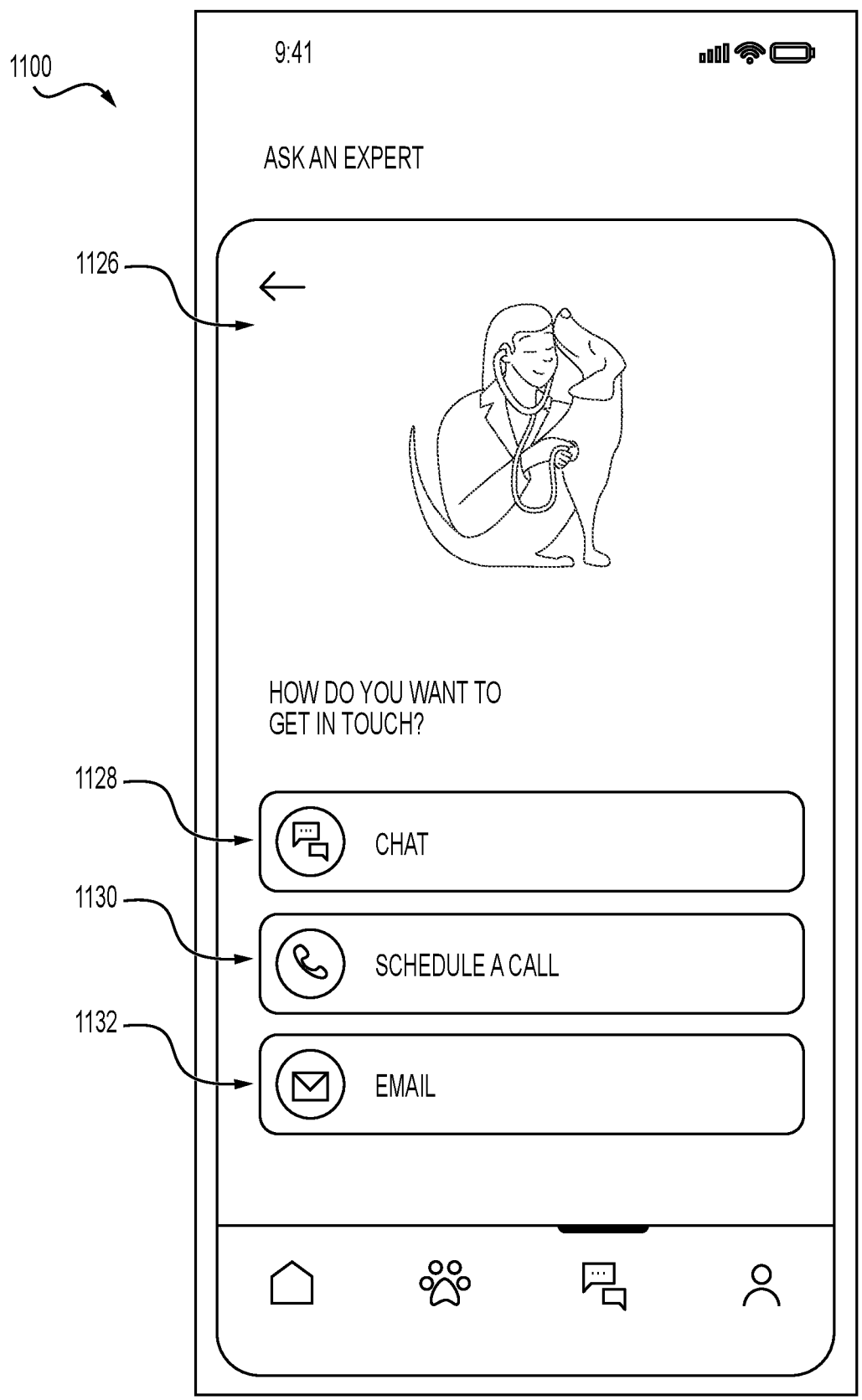

As shown in FIG. 11C, the set of expert chat screens may include a communication method screen 1126. The communication method screen 1126 may display a set of types of communication methods associated with the expert chat. For example, the communication method screen 1126 may display a first communication method icon 1128 associated with a first type of communication method, a second communication method icon 1130 associated with a second type of communication method, a third communication method icon 1132 associated with a third type of communication method, etc. The user may interact with a particular communication method icon to select a particular type of communication method associated with the expert chat.

Figure 11D:
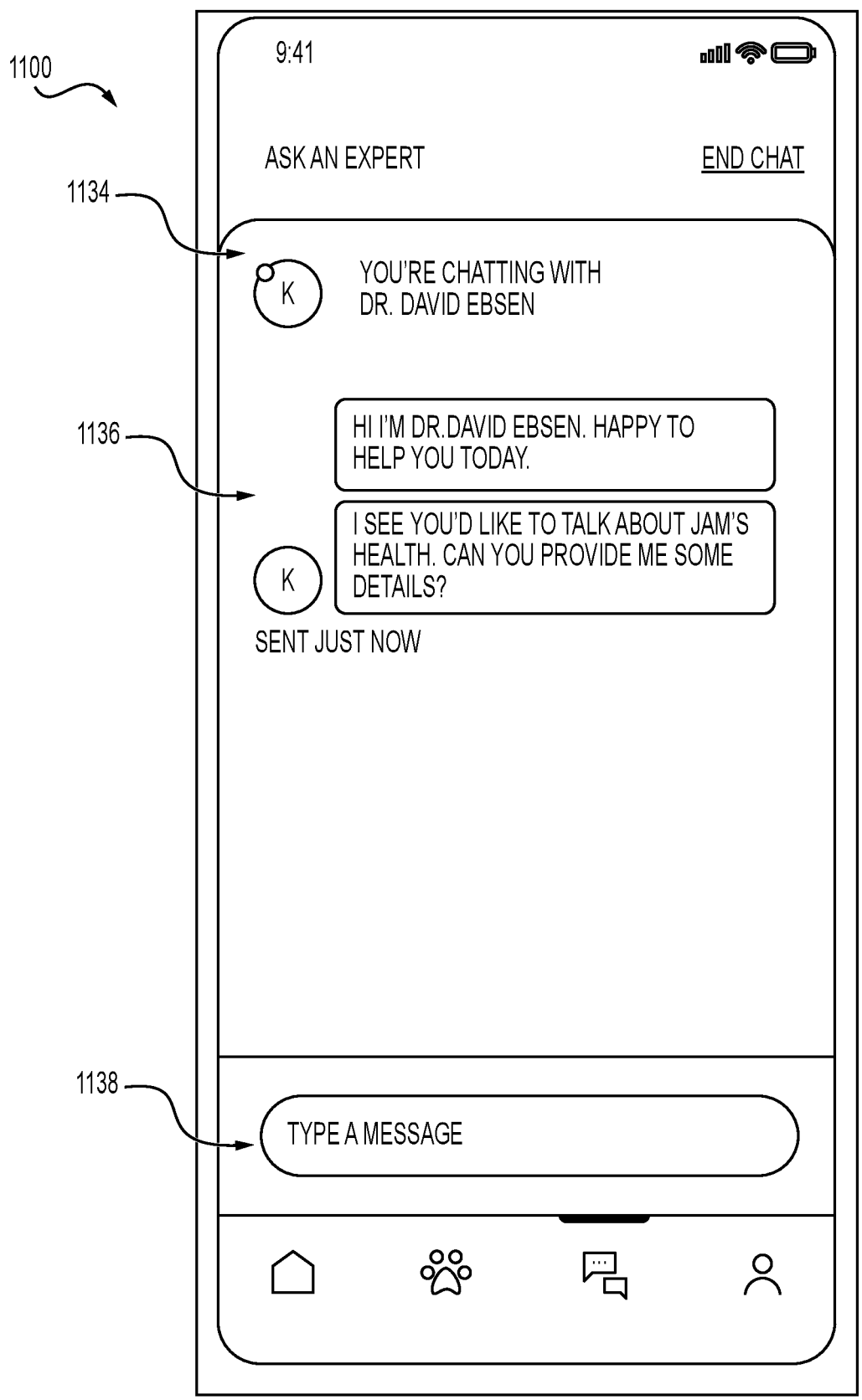

As shown in FIG. 11D, the set of expert chat screens may display a chat screen 1134. The chat screen 1134 may display a chat with a particular expert. For example, the chat screen 1134 may display messages from the expert 1136. Further, the chat screen 1134 may display a message field that permits the user to generate messages and submit the messages to the expert.

Figure 11E:
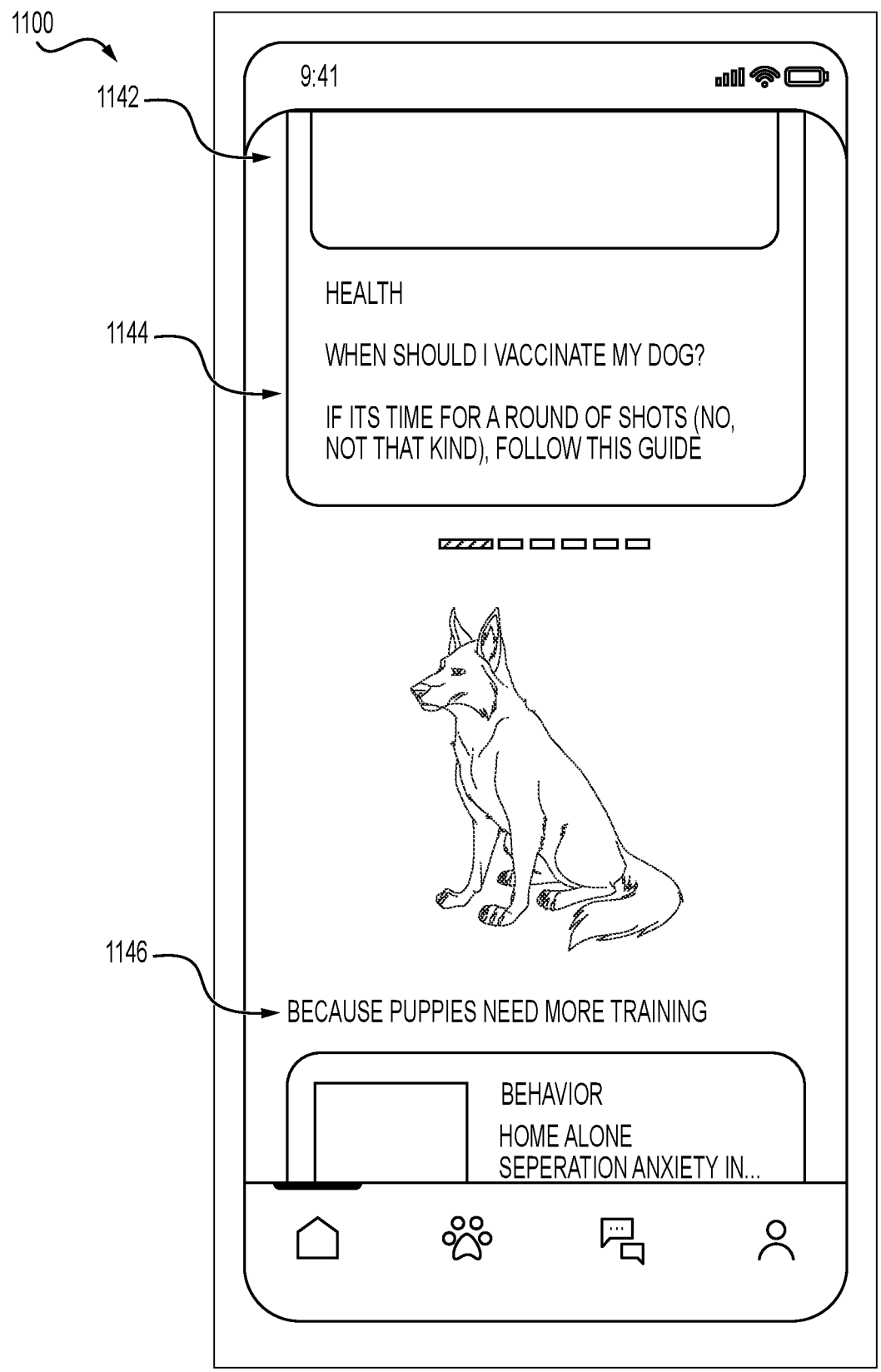
Figure 11F:
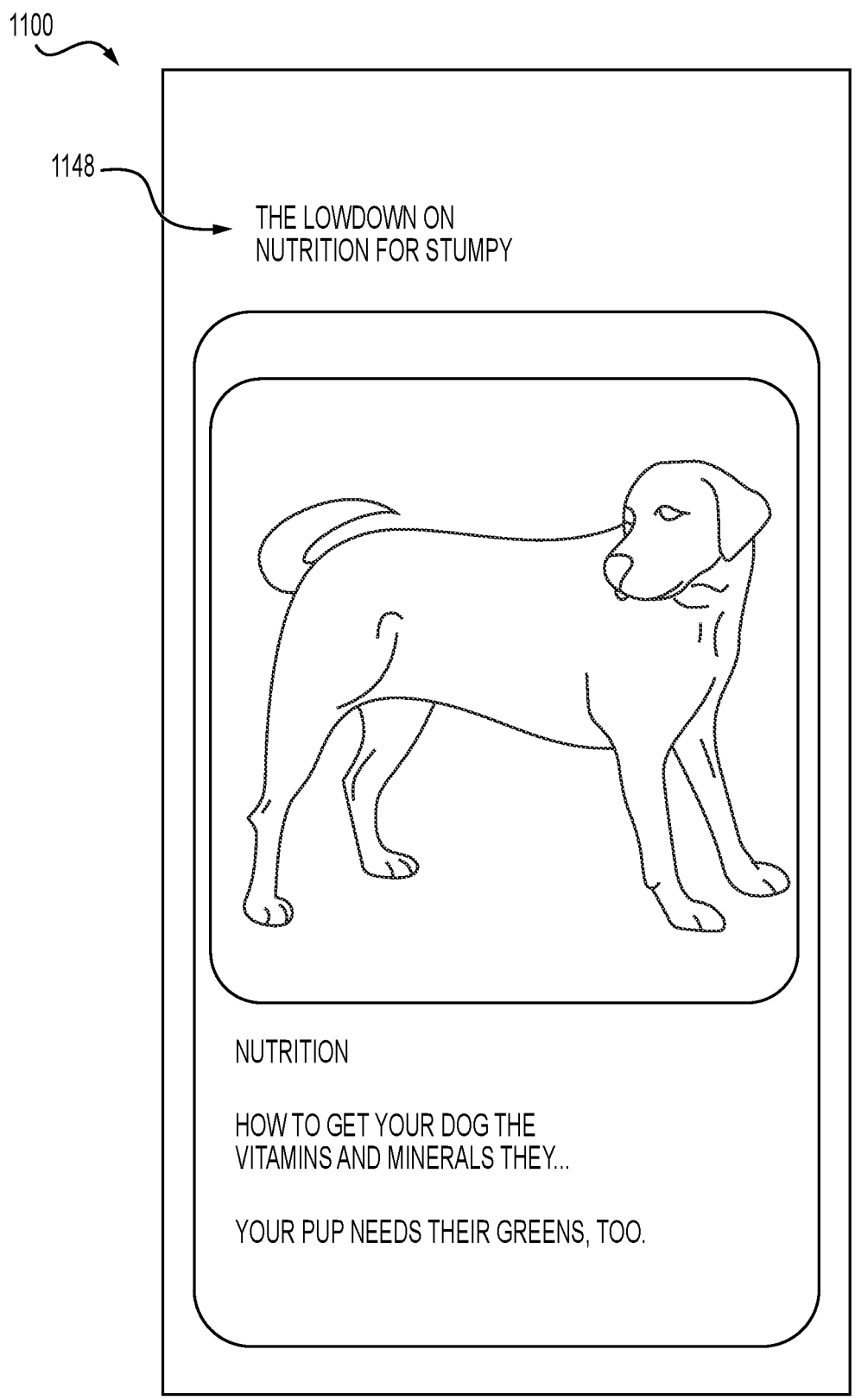

As shown in FIG. 11E, the mobile application 902 may display a content screen 1142. The content screen 1142 may display content. According to an embodiment, the content may be tailored to the user. For example, the content may be tailored to the user in accordance with the techniques described above in connection with FIGS. 3A, 3B, and 4. As shown, the content 1142 may include a first article 1144 and a second article 1146. The first article 1142 and the second article 1146 may be tailored to the user based on the chat with the expert. For example, the user might have submitted various queries to the expert related to vaccination of the pet, training of the pet, etc. In this case, the first article 1142 and the second article 1146 may be related to topics discussed with the expert. As shown in FIG. 11F, the mobile application 902 may display content 1148 that references the user's pet. Accordingly, the user might find the content to be particularly engaging and/or relevant.

Exemplary Embodiments

According to an embodiment, the platform 102 may permit a user to create an account with the platform 102. The platform 102 may receive user information, such as a name, location, etc. Additionally, or alternatively, the platform 102 may receive, from the homing system 152, pet information, such as a type, breed, age, medical condition, etc. The platform 102 may provide, to the user device 502, information associated with various external services (e.g., external services 122, 150, 162, 166, 180, and/or 190). A user may interact with the user device 502 to cause the platform 102 to search for various external services. For example, the platform 102 may search for a veterinarian based on a user input, and provide results to the user device 502 for display for the user. The user may interact with the user device 502 to select a particular external service. For example, the platform 102 may receive booking information identifying a booking of an appointment with a veterinarian based on an input by the user. In this way, the user and the pet may engage with the external service, and the platform 102 may receive information associated with the engagement. For example, the platform 102 may receive diagnosis results from the veterinarian based on the appointment, and update a pet profile with a visit summary, vaccine information, medical information, or the like. The platform 102 may provide personalized content 168 to a user device based on the updated pet profile.

According to an embodiment, the platform 102 may be configured to provide various information, services, promotions, content, etc., to a user device 502 and/or a user. For example, the platform 102 may provide a hotel concierge, travel, café access, vet check-in, instant share, product scanner, vaccine reminders, milestone reminders, product recommendations, personalized content, nutrition recommendations, document scanner, wellness recommendations, local alerts, health scores, concierge, ask-a-vet, caretaker roles, community board, lost pet service, or the like.

According to an embodiment, the pet profile 118 may include a pet biography, a location, food information, feeding information, activity information, photos, documents, weight, health history, genetics, breed, vet records, care information, or the like.

According to an embodiment, the platform 102 may provide an application (e.g., mobile application 902) to the user device 502 that permits the user device 502 to execute, or access, the application. A user of the user device 502 may establish an account for the application. The account may include various information such as the pet profile 118 and the pet owner profile 120. The application may permit the user device 502 to upload documents, and share the documents with external systems and/or services. Further, the application may permit the user device 502 to communicate with various external services. In this way, the user may communicate with various experts.

According to an embodiment, the application may include a content viewer screen. The content viewer screen may display content (e.g., articles, blog posts, etc.) that the user can consume. The content may be targeted, or tailored, to the user and/or the user's pet(s). The user may find answers to pet parenting questions through the content.

According to an embodiment, the application may include an expert chat screen that permits the user to select a particular expert to communicate with and/or to book for an appointment. The expert chat screen may display a list of the user's pet(s) for the user to select a particular pet. Based on a selection of a particular pet, the expert chat screen may display a list of potential experts (e.g., a veterinarian, a nutritionist, a behavior expert, or the like). Based on a selection of a particular expert, the application may display contact methods for which to contact the expert (e.g., chat, call, email, etc.). Based on a selection of a particular contact method, the application may display information associated with the particular contact method. For example, if the user selects a "chat" contact method, the application may establish a chat with the expert that permits the user to send various messages to the expert. As another example, if the user selects a phone call method, the application may open a phone application to call the expert. As another example, if the user select a phone call scheduling method, then the application may open a calendar application to schedule an appointment with the expert. As another example, if the user selects an email method, then the application may generate an email to send to the expert.

According to an embodiment, the application may display a pet screen. The pet screen may include information associated with a pet. For example, the pet screen may display a picture or avatar of the pet and information associated with the pet (e.g., a name, a breed, a sex, an age, or the like). Further, the pet screen may display a "gotcha date" that corresponds to a birthdate of the pet, a date on which the pet was adopted by the user, a date on which the pet was acquired by the user, or the like.

According to an embodiment, the application may provide in-app notifications as an alert mechanism to inform users when something has been changed or updated, or when the user is being prompted to take an action. Alerts might be follow-ups to a consultation or proactive actions, such as updating a profile or reminders to make an appointment.

According to an embodiment, the application may display various content for the user. For example, the application may display "general content" about caring for the pet's health and wellbeing, of what to look for in a specific expert. As another example, the application may display "local content" that is specific to a particular location (e.g., country, state, city, town, zip code, or the like). The "local content" might include lists of top experts or highlights on specific experts in the particular location. As another example, the application may display "action-prompting" content that prompts a user to take a particular action. As another example, the application may display "fun tidbits" information about the pet.

According to an embodiment, the application may display particular content. For example, the application may randomize displayed content across a larger existing general care content set. As another example, the application may curate a smaller content set that is relevant and specific to services and top areas of interest of the user. As another example, the application may mix expert-related content with general care content on a screen, and may have a separate screen for local content. As another example, the application may mix expert-related content with local content on a screen, and have a separate screen for general care content. As another example, the application may display the same content to all users regardless of the user's tenure, pet, demographics, location, or the like. As another example, the application may display tailored content corresponding to a limited set of user-provided pet characteristics. As another example, the application may display tailored content by adding in behavioral signals and user feedback mechanism. As another example, the application may display a set of content with a specific question the user can ask an expert. As another example, the application may display a set of action prompts suggesting questions that the user can ask an expert. As another example, the application may display user stage or behavior-based messages, or rotate through a set of prompts.

According to an embodiment, the application may display content having a particular structure. For example, the structure may include a title, an image, a blurb, a topic, and/or a headline.

According to an embodiment, the application may transmit various emails to the user. For example, the application may transmit a welcome email when the user creates an account with the application, a welcome subscriber email when the user subscribes to the application, a training series email, a new pet series email, a growth chart email, a gotcha day email, a new pet added email, a reset password email, or the like.

According to an embodiment, the application may display a home page screen. The home page screen may include a bottom navigation structure including a home icon, a pet identifier icon, a user profile icon, and an expert chat icon.

According to an embodiment, the application ma include a pet profile screen. The pet profile screen may display n pet profiles corresponding to the n pet(s) of the user. Each pet profile may include pet information (e.g., name, image, species, breed, age, gender, spayed/neutered status, gotcha date, weight, caretaking information, or the like), documents (e.g., health documents, vaccination records, vet records, health records, adoption certificates, obedience certificates, passports, etc.), chat summaries (e.g., a transcript of a chat), or the like.

According to an embodiment, the application may permit the user to transmit various information to another device or service. For example, the application may include a share icon that, when clicked, permits the user to select a communication method to transmit the information to another device or service.

According to another embodiment, the application may include automatic document scanning and content extraction. For example, the application may scan a document, and extract various information from the document. The application may update a pet profile using the extracted information.

Furthermore, while some embodiments described herein include some but not other features included in other embodiments, combinations of features of different embodiments are meant to be within the scope of the invention, and form different embodiments, as would be understood by those skilled in the art.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A method performed by at least one processor of a platform, the method comprising:
   receiving, by the at least one processor, a first indication that a pet owner has interacted with content related to a care topic of a pet or a second indication that the pet is experiencing a condition based on data collected by one or more external systems;
   generating, by the at least one processor, a user interface prompting the pet owner to initiate an interaction via the user interface between the pet owner and an expert related to the care topic of the pet or that has expertise related to the condition;
   receiving, from a first system by the at least one processor, a first data set associated with the interaction between the pet owner and the expert relating to the care topic of the pet or that has expertise related to the condition hosted via the first system;
   updating, by the at least one processor, pet profile data associated with the pet based on the first data set;
   determining, by the at least one processor, a portion of the pet profile data associated with a second system, the portion of the pet profile data including the first data set; and
   transmitting, by the at least one processor, the portion of the pet profile data to the second system, wherein the second system is configured to generate tailored content to provide to the pet owner based on the portion of the pet profile data.

2. The method of claim 1, wherein determining the portion of the pet profile data associated with the second system includes:
   identifying permission data of the pet owner; and
   determining the portion of the pet profile data based on the second system and the permission data.

3. The method of claim 1, wherein the first data set includes a recording of the interaction, the recording including one or more of a transcript, an audio recording, a video recording, one or more images, and notes associated with the interaction.

4. The method of claim 3, wherein the portion of the pet profile data further includes information received from one or more of:
   a device worn by the pet;
   an appliance used by the pet;
   a camera capturing images or video of the pet;
   genetic data monitoring of the pet; and
   genetic data analysis of the pet.

5. The method of claim 1, wherein the tailored content comprises at least one of an article and a product advertisement identified based on the portion of the pet profile data.

6. The method of claim 1, wherein the first data set is received in a first format of the first system, and the method further comprises:
   converting, by the at least one processor, the first data set from the first format to a second format, wherein the second format is compatible with a plurality of systems including the second system, wherein updating the pet profile data comprises updating the pet profile data associated with the pet based on the converted first data set.

7. A computer system comprising:
at least one memory having processor-readable instructions stored therein; and
at least one processor configured to access the at least one memory and execute the processor-readable instructions, which when executed by the at least one processor configure the at least one processor to perform a plurality of functions, including functions for:
receiving an indication that a pet owner has interacted with content related to a care topic of a pet;
generating, by the at least one processor, a user interface prompting the pet owner to initiate an interaction via the user interface between the pet owner and an expert related to the care topic of the pet or that has expertise related to the condition;
receiving, from a first system, a first data set associated with the interaction between the pet owner and the expert relating to the care topic of the pet or that has expertise related to the condition hosted via the first system;
updating pet profile data associated with the pet based on the first data set;
determining a portion of the pet profile data associated with a second system, the portion of the pet profile data including the first data set; and
transmitting the portion of the pet profile data to the second system, wherein the second system is configured to generate tailored content to provide to the pet owner based on the portion of the pet profile data.

8. The computer system of claim 7, wherein determining the portion of the pet profile data associated with the second system includes:
identifying permission data of the pet owner; and
determining the portion of the pet profile data based on the second system and the permission data.

9. The computer system of claim 7, wherein the first data set includes a recording of the interaction, the recording including one or more of a transcript, an audio recording, a video recording, one or more images, and notes associated with the interaction.

10. The computer system of claim 7, wherein the content comprises at least one of an article and a product advertisement identified based on the portion of the pet profile data.

11. The computer system of claim 7, wherein the first data set is received in a first format of the first system, and wherein the plurality of functions further include:
converting the first data set from the first format to a second format, wherein the second format is compatible with a plurality of systems including the second system,
wherein updating the pet profile data comprises updating the pet profile data associated with the pet based on the converted first data set.

12. A non-transitory computer-readable medium storing instructions that, when executed by at least one processor, configure the at least one processor to perform:
receiving an indication that a pet owner has interacted with content related to a care topic of a pet;
generating, by the at least one processor, a user interface prompting the pet owner to initiate an interaction via the user interface between the pet owner and an expert related to the care topic of the pet or that has expertise related to the condition;
receiving, from a first system, a first data set associated with the interaction between the pet owner and the expert relating to the care topic of the pet or that has expertise related to the condition hosted via the first system;
updating pet profile data associated with the pet based on the first data set;
determining a portion of the pet profile data associated with a second system, the portion of the pet profile data including the first data set; and
transmitting the portion of the pet profile data to the second system, wherein the second system is configured to generate tailored content to provide to the pet owner based on the portion of the pet profile data.

13. The non-transitory computer-readable medium of claim 12, wherein determining the portion of the pet profile data associated with the second system includes:
identifying permission data of the pet owner; and
determining the portion of the pet profile data based on the second system and the permission data.

14. The non-transitory computer-readable medium of claim 12, wherein the first data set includes a recording of the interaction, the recording including one or more of a transcript, an audio recording, a video recording, one or more images, and notes associated with the interaction.

15. The non-transitory computer-readable medium of claim 12, wherein the content comprises at least one of an article and a product advertisement identified based on the portion of the pet profile data.

16. The non-transitory computer-readable medium of claim 12, wherein the first data set is received in a first format of the first system, and wherein the instructions further configure the at least one processor to perform:
converting, by the at least one processor, the first data set from the first format to a second format, wherein the second format is compatible with a plurality of systems including the second system,
wherein updating the pet profile data comprises updating the pet profile data associated with the pet based on the converted first data set.

* * * * *